US011246786B2

(12) United States Patent
Tsui et al.

(10) Patent No.: US 11,246,786 B2
(45) Date of Patent: Feb. 15, 2022

(54) POWER ASSISTIVE DEVICE FOR HAND REHABILITATION AND A METHOD OF USING THE SAME

(71) Applicant: REHAB-ROBOTICS COMPANY LTD., Hong Kong (CN)

(72) Inventors: Kam Fai Michael Tsui, Hong Kong (CN); Haris Begovic, Hong Kong (CN); Pui Yung Tsui, Hong Kong (CN); Wai Chiu Or, Hong Kong (CN); Pak Hin Leung, Hong Kong (CN)

(73) Assignee: REHAB-ROBOTCS COMPANY LTD., Hong Kong (CN)

( * ) Notice: Subject to any disclaimer, the term of this patent is extended or adjusted under 35 U.S.C. 154(b) by 802 days.

(21) Appl. No.: 15/387,666

(22) Filed: Dec. 22, 2016

(65) Prior Publication Data
US 2018/0177666 A1    Jun. 28, 2018

(51) Int. Cl.
*A61H 1/00*    (2006.01)
*A61F 5/01*    (2006.01)
*A61H 1/02*    (2006.01)

(52) U.S. Cl.
CPC .......... *A61H 1/0288* (2013.01); *A61F 5/013* (2013.01); *A61F 2005/0144* (2013.01);
(Continued)

(58) Field of Classification Search
CPC .............. A61F 2005/0146; A61F 5/013; A61F 2005/0144; A61F 2005/0155;
(Continued)

(56) References Cited

U.S. PATENT DOCUMENTS 5,372,597 A    12/1994 Hotchkiss et al.
5,662,595 A    9/1997 Chesher
(Continued)

FOREIGN PATENT DOCUMENTS

CN    201164564 Y    12/2008
CN    101433491    5/2009
(Continued)

OTHER PUBLICATIONS

Begovic Haris, Zhou Guang-Quan, Li Tianjie, Wang Yi, Zheng Yong-Ping, Detection of the electromechanical delay and its components during voluntary isometric contraction of the quadriceps femoris muscle, Dec. 23, 2014, Frontiers in Physiology, vol. 5 pp. 494 (Year: 2014).*

(Continued)

*Primary Examiner* — Bradley H Philips
*Assistant Examiner* — Savannah L Gabriel
(74) *Attorney, Agent, or Firm* — Eagle IP Limited; Jacqueline C. Lui

(57) ABSTRACT

A power assistive device for hand rehabilitation that provides training of a combined movement of finger flexion-extension and forearm supination-pronation to a user. The power assistive device includes a hand brace and a base. The hand brace includes finger assemblies that adjustably connect to a platform, actuators that connect to the finger assemblies, and strain gauge sensors that connect to the finger assemblies and detect force signals generated by movement of the finger assemblies. The base removably connects to the hand brace and includes a forearm support, a C-shaped ring that includes C-shaped tracks formed along an inner circumferential surface of the C-shaped ring, a rotatable platform that moves along the C-shaped tracks, a mounting platform that connects to the rotatable platform, and an electromyography (EMG) sensor that attaches to the
(Continued)

forearm of the user and senses EMG signals generated by movement of the hand of the user.

5 Claims, 27 Drawing Sheets

(52) U.S. Cl.
CPC ............. *A61F 2005/0155* (2013.01); *A61H 2201/1638* (2013.01); *A61H 2201/5061* (2013.01); *A61H 2201/5064* (2013.01); *A61H 2205/065* (2013.01); *A61H 2205/067* (2013.01); *A61H 2230/605* (2013.01)

(58) Field of Classification Search
CPC ............. A61H 1/027; A61H 1/0274; A61H 2001/0203; A61H 1/0288; A61H 2201/1635; A61H 2201/5061; A61H 2230/605; A61H 2205/065; A61H 2205/067; A61H 2201/5064; A61H 2201/5092; A61B 5/04004; A61B 5/0488
USPC .......................................................... 601/40
See application file for complete search history.

(56) References Cited

U.S. PATENT DOCUMENTS

| | | | |
|---|---|---|---|
| 5,759,165 A | 6/1998 | Malewicz | |
| 5,951,499 A | 9/1999 | Saringer et al. | |
| 6,506,172 B1 | 1/2003 | Hepburn et al. | |
| 6,743,187 B2 | 6/2004 | Solomon et al. | |
| 7,537,547 B1 | 5/2009 | Hosick | |
| 7,618,381 B2 | 11/2009 | Krebs et al. | |
| 8,574,178 B2* | 11/2013 | Tong | A61H 1/0285 601/40 |
| 8,849,453 B2 | 9/2014 | Bergelin et al. | |
| 2004/0082885 A1 | 4/2004 | Culhane et al. | |
| 2009/0192420 A1 | 7/2009 | Armstrong et al. | |
| 2009/0259338 A1* | 10/2009 | Tong | A61H 1/0274 700/258 |
| 2010/0305717 A1* | 12/2010 | Tong | A61H 1/0285 623/64 |
| 2013/0030327 A1 | 1/2013 | Zhang et al. | |
| 2013/0041477 A1* | 2/2013 | Sikdar | A61B 8/085 623/57 |
| 2013/0261514 A1* | 10/2013 | Tsui | A61H 1/0288 601/40 |
| 2014/0194799 A1 | 7/2014 | Bonutti et al. | |
| 2015/0112451 A1* | 4/2015 | Dechev | A61F 2/54 623/63 |
| 2015/0148728 A1* | 5/2015 | Sallum | A61F 5/10 602/22 |
| 2015/0245972 A1* | 9/2015 | Arakawa | A61H 1/0288 601/40 |
| 2015/0374575 A1* | 12/2015 | Kamper | A61H 1/0288 601/40 |
| 2016/0058644 A1* | 3/2016 | Cheatham, III | A61H 1/008 601/84 |
| 2016/0143751 A1* | 5/2016 | Chestek | A61F 2/72 623/25 |
| 2016/0220808 A1* | 8/2016 | Hyde | A61N 1/0452 |
| 2016/0287422 A1 | 10/2016 | Kelly et al. | |

FOREIGN PATENT DOCUMENTS

| | | |
|---|---|---|
| CN | 101978940 A | 2/2011 |
| CN | 102274107 A | 12/2011 |
| CN | 104107134 A | 10/2014 |
| CN | 104306134 | 1/2015 |
| CN | 104337666 A | 2/2015 |
| CN | 104665962 A | 6/2015 |
| CN | 104706502 A | 6/2015 |
| CN | 105476809 | 4/2016 |
| CN | 105726263 | 7/2016 |
| CN | 105796285 A | 7/2016 |
| CN | 105853146 | 8/2016 |
| CN | 106074092 | 11/2016 |
| CN | 106109165 | 11/2016 |
| TW | M530168 | 10/2016 |

OTHER PUBLICATIONS

Walker, Owen, Rate of Force Development (RFD), Mar. 9, 2016 (Year: 2016).*
Peternel et al., "Adaptive Control of Exoskeleton Robots for Periodic Assistive Behaviours based on EMG Feedback Minimisation", Feb. 16, 2016 (Year: 2016).*
Kiguchi et al. "An EMG-Based Control for an Upper-Limb Power-Assist Exoskeleton Robot", IEEE Transactions On Systems, Man, and Cybernetics—Part B: Cybernetics, vol. 42, No. 4, Aug. 2012 (Year: 2012).*
Maffiuletti et al. "Rate of force development: physiological and methodological considerations", Eur J Appl Physiol (2016) 116:1091-1116, Mar. 3, 2016 (Year: 2016).*
Kras Borges C, Rodrigues AM, Loss JF, Petersen RDS and Oliveira MA, Effects of Elbow Joint Position on Forearm Supination Torque Control Among Young Adults, Rev. bras, fisioter., Sao Carlos, v.11, n.6, pp. 487-493, Nov./Dec. 2007.
Cagatay Barut, Hasan B. Turgut, Evaluation of Muscle Activities during Locking-Unlocking Movements, Neurosciences 2006, vol. 11(3), pp. 150-157.
R.A.R.C. Gopura, Kazuo Kiguchi and Etsuo Horikawa, A Study on Human Upper-Limb Muscles Activities during Daily Upper-Limb Motions, International Journal of Bioelectromagnetism, vol. 12, No. 2, pp. 54-61, 2010.
Begovic H, et al. (2014) Detection of the electromechanical delay and its components during voluntary isometric contraction of the quadriceps femoris muscle. Front Physiol. Dec. 23, 2014;5:494.

* cited by examiner

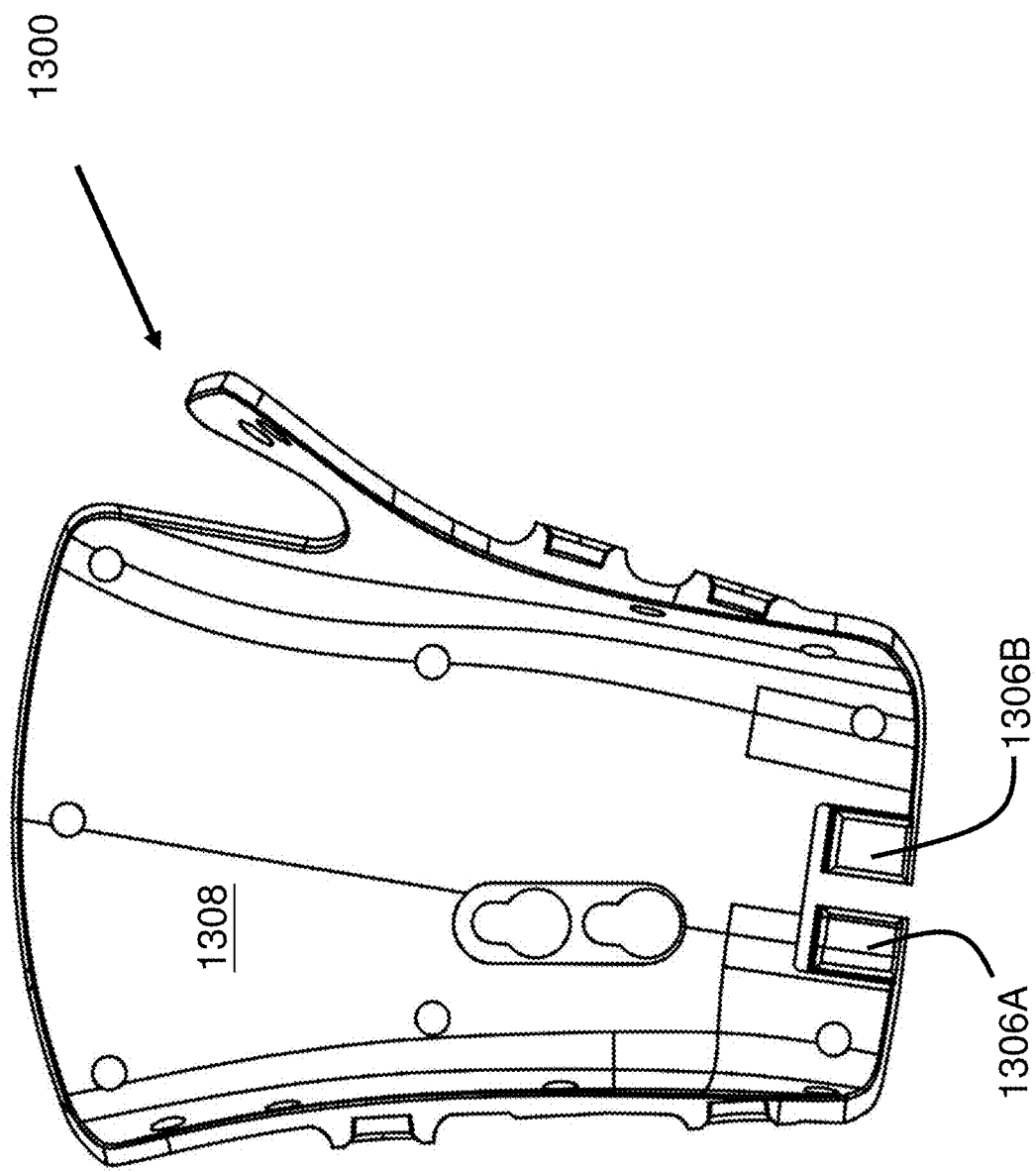

POWER ASSISTIVE DEVICE FOR HAND REHABILITATION AND A METHOD OF USING THE SAME

FIELD OF THE INVENTION

The present invention relates to a power assistive device for hand rehabilitation that provides training of finger flexion-extension and forearm supination-pronation to a user.

BACKGROUND

Power assistive devices have been widely used for hand rehabilitation. These devices often include a single sensor and provide training in a single degree of freedom. It may not be efficient and effective to use these devices to perform different types of training exercises.

In view of the demand for efficiently providing comprehensive trainings for hand rehabilitation, improvements in power assistive devices are desired.

SUMMARY OF THE INVENTION

One example embodiment is a power assistive device for hand rehabilitation that provides training of finger flexion-extension and forearm supination-pronation to a user. The power assistive device includes a hand brace and a base. The hand brace attaches to a hand of the user and includes a plurality of finger assemblies that adjustably connect to a platform and that attach to fingers of the user, a plurality of actuators that connect to the finger assemblies and that actuate the finger assemblies, and a plurality of strain gauge sensors that connect to the finger assemblies and that detect force signals generated by movement of the finger assemblies. The base removably connects to the hand brace and includes a forearm support that is located on a proximal end of the base and that receives a forearm of the user, a C-shaped ring that abuts the forearm support and that includes a plurality of C-shaped tracks formed along an inner circumferential surface of the C-shaped ring, a rotatable platform that moves along the C-shaped tracks and that receives a forearm of the user, a mounting platform that connects to and extends from a distal end of the rotatable platform and that removably mounts the hand brace onto the base, and an electromyography (EMG) sensor that attaches to the forearm of the user and that senses EMG signals generated by movement of the hand of the user, in which the EMG signals and the force signals are used to provide the training of the finger flexion-extension and the forearm supination-pronation to the user.

Other example embodiments are discussed herein.

BRIEF DESCRIPTION OF THE DRAWINGS

FIG. 13B shows an inner view of a hand brace platform in accordance with an example embodiment.

DETAILED DESCRIPTION

Figure 1A:
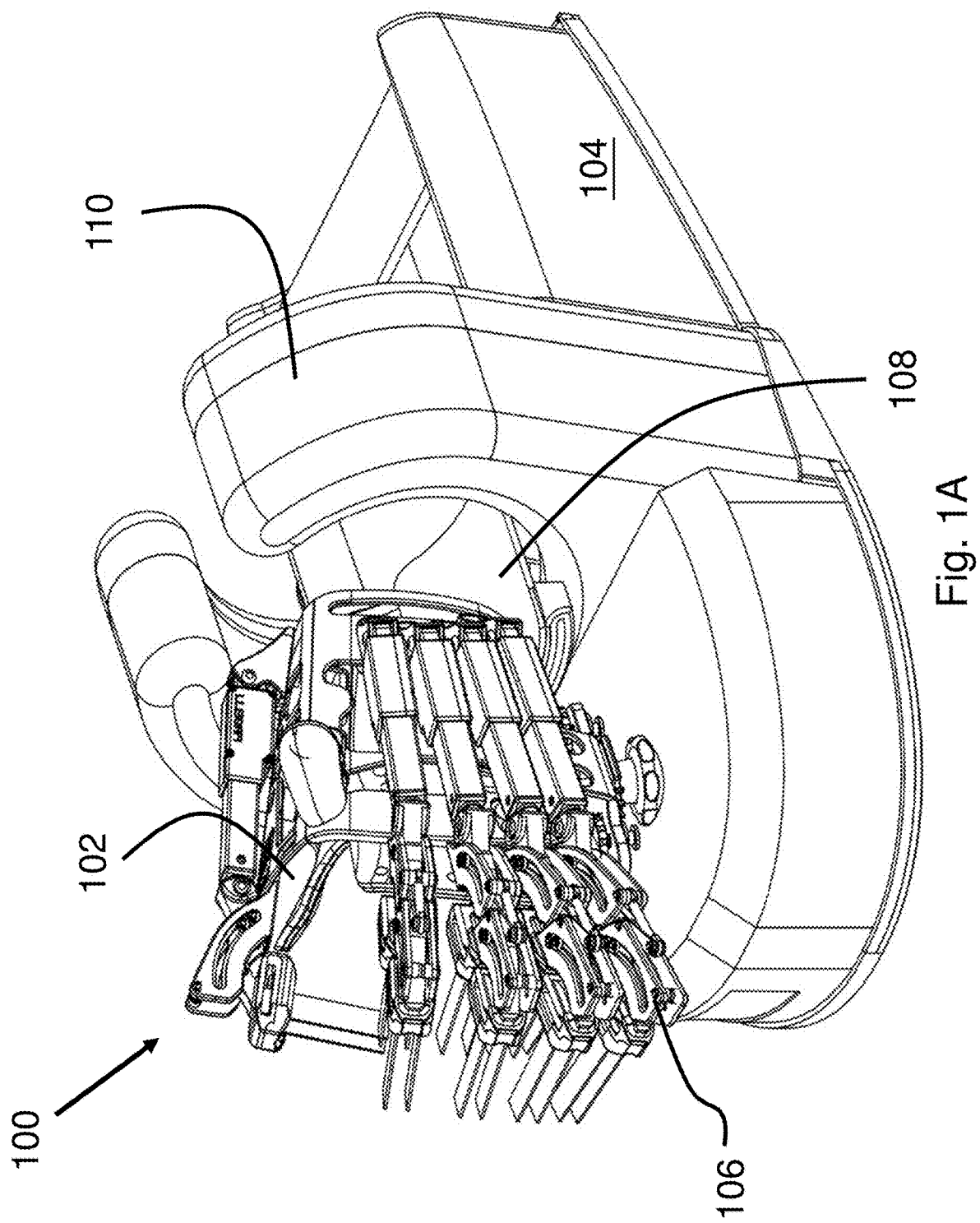
FIG. 1A shows a left perspective view of a power assistive device in accordance with an example embodiment.

Example embodiments relate to apparatus and method that provide training of finger flexion-extension and forearm supination-pronation to a user.

The use of surface electromyography (EMG) in a power assistive device for hand rehabilitation can provide important information on a motor unit neural activation and control in patients. The muscle fiber conduction velocity and EMG amplitude are two relevant parameters in surface EMG signal detection and processing. Meanwhile, mechanomyography (MMG) is useful as a non-invasive means to study muscle contractility in humans. Muscle contraction is accompanied by dimensional changes of the transverse diameter of the muscle fibers. These dimensional changes generate "in vivo" muscle surface oscillations, recordable by an appropriate probe placed over the muscle. When several motor units are active, a summation of surface oscillations generates a signal that has been labeled as surface MMG.

When an EMG sensor, an MMG sensor, and a strain gauge sensor are combined and processed synchronously, unique information about the electro-mechanical properties and motor control strategies during several types of muscle contractions can be acquired. When muscle is contracted the onset of each one of these comes in a physiological order in which EMG signals are the first, followed by MMG signals with force signals being the last to come. Even though the signal processing of all these three signals are carefully done, time delay between EMG signals and force signals with an onset of MMG in between, is usually around 40-50 milliseconds (ms). This is a very small time range but since all these three signals are incorporated and have very close onsets to each other, this time range can represent a real onset time of the muscle contraction. Such a precise measurement of the onset of the muscle contraction can provide unique information for robotic rehabilitation for patients. Reaction time measurement as a very relevant measurement parameter in robotics should be measured with a precise detection of muscle contraction onset, which can be made possible with integration of three sensors, e.g., EMG sensors, MMG sensors, and strain gauge sensors. For robotic purposes, even much larger time delays can be considered as an onset once the reliability (particularly Inter-Correlation-Coefficient) or repeatability without significant differences between measurements is shown to be under influence of many external factors.

One example embodiment includes a hand brace, a base that removably connects to the hand brace, and an EMG sensor that attaches to an upper arm/forearm of the user and senses EMG signals generated by hand movement of the user.

In one example embodiment, the EMG sensor also includes an MMG sensor and sense both EMG and MMG signals generated by hand movement of the user.

In an example embodiment, the hand brace includes finger assemblies, actuators that connect to the finger assemblies and actuate the finger assemblies, strain gauge sensors that connect to the finger assemblies and detect force signals generated by movement of the finger assemblies.

The base includes a forearm support located on a proximal end of the base, a C-shaped ring abuts the forearm support and includes C-shaped tracks formed along an inner circumferential surface of the C-shaped ring, a rotatable platform that runs along the C-shaped tracks, and a mounting platform that connects to and extends from a distal end of the rotatable platform.

An example embodiment includes a hand rehabilitation system that provides training of flexion-extension of fingers and supination-pronation of a forearm to a user. The system includes a hand brace that is wearable by the user and that includes an external platform and an internal platform that connects to the external platform, a finger assembly that movably mounts on the internal platform of the hand brace, a forearm base that removably connects to the hand brace, an EMG sensor that attaches to the upper arm/forearm of the user and detects EMG signals of the upper arm/forearm of the user, and a processor that connects to the hand brace and the forearm base.

In one example embodiment, the EMG sensor also includes an MMG sensor and sense both EMG and MMG signals of the forearm of the user.

In one example embodiment, the finger assembly includes an actuator that actuates the finger assembly and a strain gauge sensor that connects to the finger assembly. The strain gauge sensor detects force signals of the finger of the user.

In another example embodiment, the forearm base includes a front end portion that locates on a distal end of the forearm base, a rear end portion that locates on a proximal end of the forearm base, and a C-shaped ring that locates between the front end portion and the rear end portion. The C-shaped ring opens upwards and includes a C-shaped track that is formed along an inner circumferential surface of the C-shaped ring, a rotatable platform that rotates along the C-shaped track, and an L-shaped mounting platform that extends from a distal end of the rotatable platform. The rotatable platform receives and supports a forearm of the user. The L-shaped mounting platform removably receives the hand brace such that the hand brace removably mounts on the forearm base. The processor receives and analyzes the EMG signals the force signals to determine an onset time of muscle dynamics of the hand of the user, so as to provide the training to the user.

In another example embodiment, the processor receives and analyzes the EMG signals, the MMG signals, and the force signals to determine an onset time of muscle dynamics of the hand of the user, so as to provide the training to the user.

In one example embodiment, the rotatable platform rotates between a maximum supination position and a maximum pronation position. The rotatable platform supinates from a neutral position (i.e. a position where a thumb of the user faces upwards and is regarded as 0 degree) to a maximum of 45 degrees of supination (to an outer side) with respect to the neutral position at the maximum supination position. The rotatable platform pronates from the neutral position to a maximum of 90 degrees of pronation (to an inner side) with respect to the neutral position at the maximum pronation position.

In another example embodiment, the forearm base further includes a locking knob that screwably connects to the L-shaped mounting platform. Further, the locking knob adjustably mounts the hand brace onto the L-shaped mounting platform to fix a wrist of the user at three different positions when the user wears the hand brace and puts the forearm on the rotatable platform.

In one example embodiment, when the wrist is fixed at a first wrist extension position, the wrist rests at a neutral position of 0 degrees with respect to a longitudinal axis of the forearm of the user. When the wrist is fixed at a second wrist extension position, the wrist extends 15 degrees with respect to the longitudinal axis. When the wrist is fixed at a third wrist extension position, the wrist extends 30 degrees with respect to the longitudinal axis.

In an example embodiment, the forearm base includes a position tracking sensor that tracks a movement route of the user on moving the forearm base. In another example embodiment, the forearm base includes an emergency stop button that enables the user to stop the forearm base from operation to protect the user in case any unexpected malfunction of any part of the forearm base.

In one example embodiment, the system includes a wireless receiver that receives commands from a smartphone, tablet, or other portable electronic device. By way of example, commands include actuating the finger assembly for bending and extending fingers of the user, and rotating the rotatable platform along the C-shaped track for supinating and pronating the forearm of the user.

In an example embodiment, the EMG sensor is an EMG-MMG sensor that includes two EMG electrodes and a MMG sensor. The two EMG sensors are 20 millimeters (20 mm)

apart and sense the EMG signals. The MMG sensor locates between the two EMG electrodes and senses MMG signals.

In an example embodiment, a method to determine an onset time of muscle dynamics involves implementation of three different sensors, namely an EMG sensors, an MMG sensors, and a strain gauge sensors. An EMG onset time, an MMG onset time and a force onset time are determined from EMG signals sensed by the EMG sensors, MMG signals sensed by the MMG sensors and force signals sensed by the strain gauge sensors respectively. Time delays between the EMG onset times, the MMG onset times and the force onset times are then calculated and an average point will be considered as a real onset time of muscle dynamics, while voluntary movement is intended to be generated by the user.

By way of example, there are two EMG sensors applied in which one of the EMG sensors senses EMG signals for finger flexion and the other EMG sensor senses EMG signals for finger extension. There are also two MMG sensors applied in which one of the MMG sensors senses MMG signals for finger flexion and the other MMG sensor senses MMG signals for finger extension. Further, there are five strain gauge sensors applied in which each of the strain gauge sensors senses force signals of each of the fingers of the user.

In another example embodiment, there are two EMG sensors applied in which one of the EMG sensors senses EMG signals for forearm supination and the other EMG sensor senses EMG signals for forearm pronation. There are also two MMG sensors applied in which one of the MMG sensors senses MMG signals for forearm supination and the other MMG sensor senses MMG signals for forearm pronation. Further, there are five strain gauge sensors applied in which each of the strain gauge sensors senses force signals of each of the fingers of the user.

In an example embodiment, four parameters, namely T0, T1, T2, and rate of force development (RFD) are parameters in determining the time relationship of a complete muscle dynamics. By way of example, T0 is a time when an external stimulus applies to the system. T1 is an onset time of muscle dynamics and determined by a mid-time that is a time halfway between the EMG onset time and the force onset time.

In one example embodiment, T1, the onset time of muscle dynamics, is determined by either a first average time between the EMG onset time and the force onset time, or a second average time between the MMG onset time and the force onset time. The choice of using either the first average time or the second average time as T1 depends on whether the EMG signals or the MMG signals are sensed first. If the EMG signals are sensed first, the first average time will be T1, while in case the MMG signals are sensed first, the second average time will be T1. By way of example, EMG signals are generally sensed earlier than the MMG signals.

By way of example, T2 is an onset time of muscle force threshold and is determined when the force exceeds a force threshold, for example, 5 Newtons (N) or 10 N. RFD is the rate of change or development of the force calculated starting from the force onset time to the force threshold.

As one example, an EMG signal threshold and/or a force signal threshold can be set as the muscle force threshold. In one example embodiment, the EMG signal muscle force threshold is set as the muscle force threshold at an acute stage after stroke. In another example embodiment, the force signal threshold is set as the muscle force threshold at a more chronic stage after stroke or when marked improvement can be seen and the patient is able to steer the force, for example, to manipulate an object.

Figure 1B:
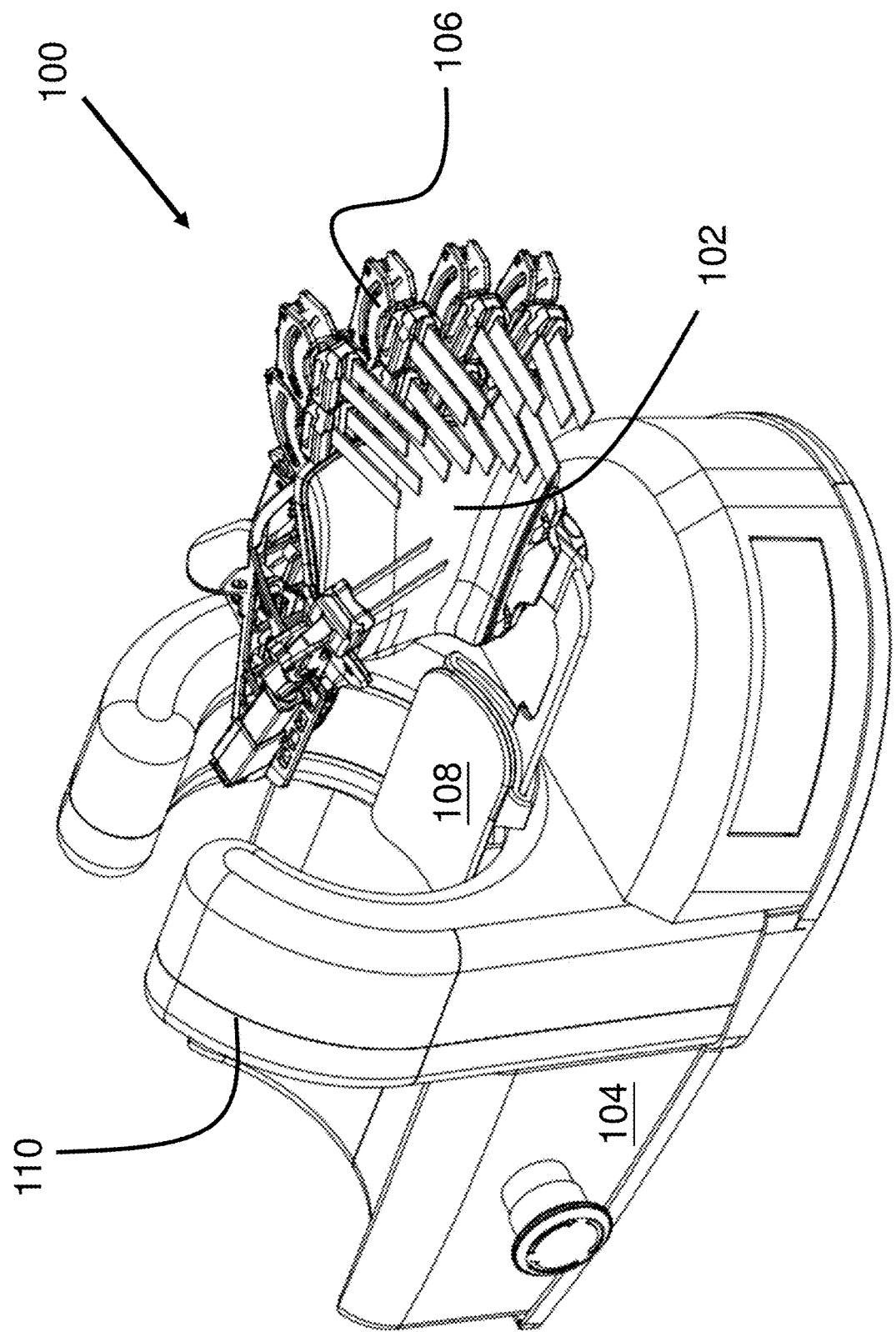
FIG. 1B shows right perspective view of a power assistive device in accordance with an example embodiment.
Figure 1C:
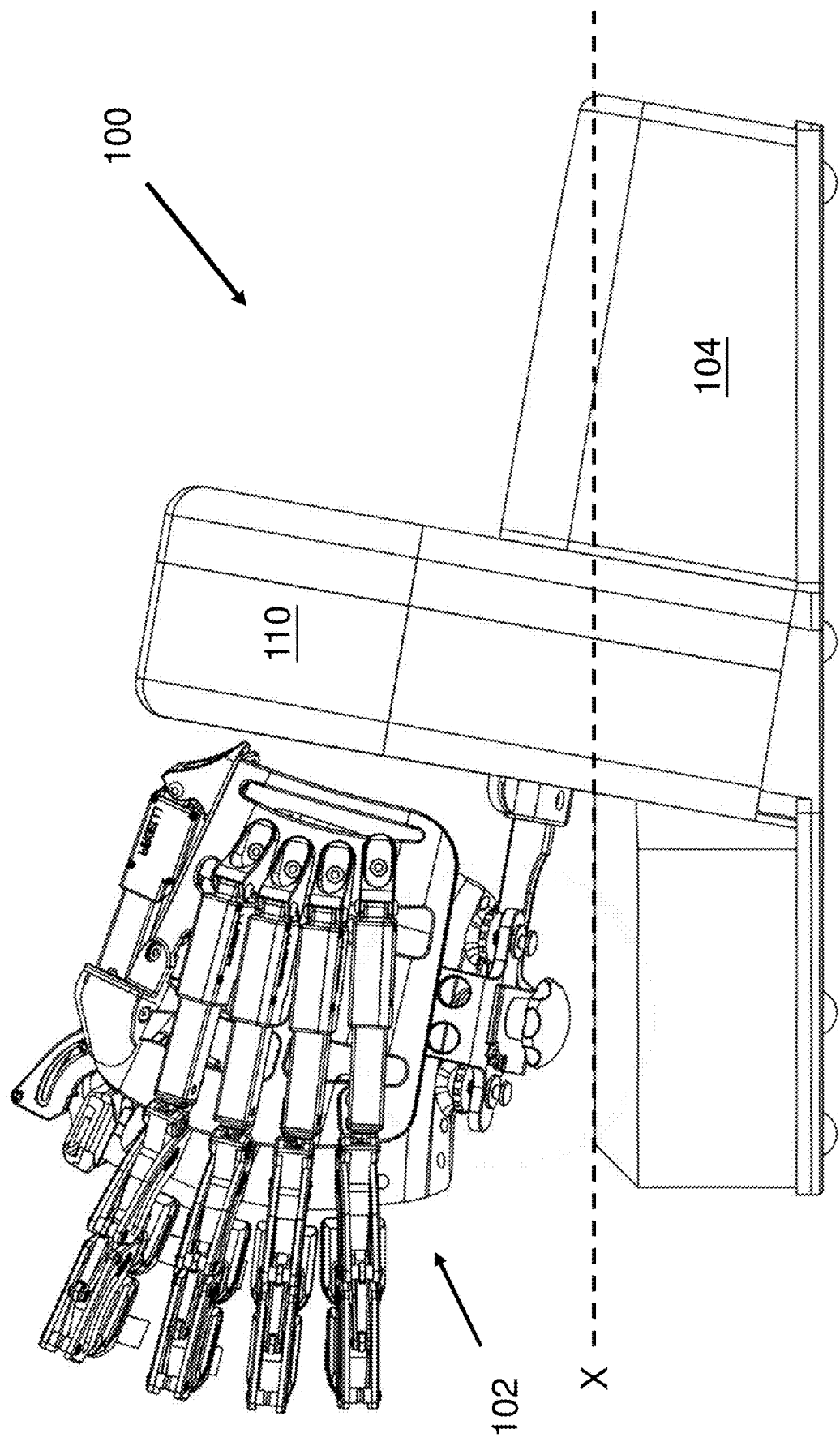
FIG. 1C shows a left side view of a power assistive device in accordance with an example embodiment.

FIGS. 1A-1C show a power assistive device 100 (hereinafter the "device") that is used for hand rehabilitation in accordance with an example embodiment. The device 100 includes a hand brace 102 that removably connects to a base 104. A user suffering from upper-limb motor disability or upper-limb paralysis, or a stroke patient, can insert an affected hand into the hand brace 102 and rest a forearm of the affected hand on the base 104 for hand rehabilitation. By way of example, hand rehabilitation includes training of finger flexion-extension and forearm supination-pronation. In one embodiment, the device 100 is driven by electromyography (EMG) signals of the affected limb of the user, in which the EMG signals reflect an intention of the user to move the affected limb.

In an example embodiment, the hand brace 102 mounts on the base 104 at an inclination angle of ten degrees with respect to an axis X as shown in FIG. 1C. Under this inclination angle, a user can place his hand on the base in a natural position with minimal stress to his wrist joint on wearing the device 100.

FIGS. 2A-2D show a hand brace 200 of the device in accordance with an example embodiment. The hand brace 200 includes an external platform 202, an internal platform 204 that connects to an inner surface of the external platform 202, a plurality of finger assemblies 206 that adjustably connect to the external platform 202 and the internal platform 204, a plurality of actuators 208 that moveably connect to the finger assemblies 206, a plurality of actuator bases 210 that are fixed on an outer surface of the external platform 202 and connects to the actuators 208, and a side fixation bracket 212 that adjustably connect to the external platform 202 and the internal platform 204.

By way of example, the hand brace includes five finger assemblies that adjustably connect to the external platform and the internal platform, five actuators that moveably connect to the five finger assemblies respectively, and five actuator bases that are fixed on the outer surface of the external platform and connect to the five actuators respectively. The five actuators actuate the five finger assemblies respectively.

In an example embodiment, upon wearing the hand brace 200, a dorsal side of a hand of the user is in contact with an inner side of the internal platform 204. By way of example, the internal platform 204 can be of different sizes to accommodate palms with different sizes.

In one example embodiment, the finger assembly 206 movably mounts on the inner surface of the external platform 202 and extends outwardly from a distal end 214 of the external platform 202. The finger assembly 206 includes an intermediate rail guide 224 at the distal end 214, a proximal rail guide 226 at a proximal end 220, an intermediate follower assembly 216 that connects the intermediate rail guide 224 and the proximal rail guide 226, and a proximal follower assembly 218 that connects the proximal rail guide 226 to the actuator 208. A front finger follower 256 connects to the intermediate follower assembly 216. The intermediate follower assembly 216 and the proximal follower assembly 218, respectively, ensures a controlled and proportioned angular rotation in a restricted range of a proximal interphalangeal (PIP) joint and a metacarpophalangeal (MCP) joint of the user, such that a movement and responsiveness of the hand brace 200 resembles a cohesive movement of a human finger specifically for hand opening action and hand grasping action.

In one example embodiment, a strain gauge sensor 232 is disposed on the front finger follower 256.

In an example embodiment, each of the intermediate rail guide 224 and the proximal rail guide 226 has an arc-shaped track 228. Bearings 230 are movably disposed within the track 228 so that the front finger follower 256 as driven by the intermediate follower assembly 216 and the proximal follower assembly 218, respectively, follow a path of the intermediate rail guide 224 along the track 228 and a path of the proximal rail guide 226 along the track 228. By way of example, a rotational range of the intermediate rail guide 224 and a rotational range of the proximal rail guide 226 are different, such that the intermediate follower assembly 216 and the proximal follower assembly 218 generate a proportional relationship between the intermediate rail guide 224 and the proximal rail guide 226. In one example embodiment, the hand brace 200 has a linkage assembly 222 that connects the intermediate follower assembly 216 and the proximal rail guide 226.

In one example embodiment, an intermediate strap holder 246 connects to a bottom side of the front finger follower 256, and a proximal strap holder 248 connects to a bottom side of the intermediate rail guide 224 and a bottom side of the proximal follower assembly 218. The intermediate strap holder 246 adjustably fixes a finger strap 250 through a strap position adjustable slot 252 that is disposed within a cavity of the intermediate strap holder 246. Likewise, the proximal strap holder 248 adjustably fixes a finger strap 250 through a strap position adjustable slot 252 that is disposed within a cavity of the proximal strap holder 248. By way of example, the intermediate strap holder 246 and the proximal strap holder 248 are made of soft pad. The finger strap 250 warps around the finger of the user to hold the finger within the finger assembly 206 and keep the finger in contact while the finger assembly 206 is moving.

The actuator 208 has a proximal end that connects to proximal end 220 of the external platform 202 through the actuator bases 210, and a distal end that connects to the proximal follower assembly 218. When the actuator 208 is actuated, a longitudinal motion of the actuator 208 is translated into an angular/rotational motion that causes relative rotation of the proximal follower assembly 218 along the track 228 of the proximal rail guide 226. The rotational movement of the proximal follower assembly 218 then actuates a rotational movement of the intermediate rail guide 224 in which when the intermediate rail guide 224 rotates, the intermediate follower assembly 216 rotates and pushes the front finger follower 256 to rotate along the track 228.

In one example embodiment, the hand brace 200 has a thumb platform 234 that is formed separately or integrally with the external platform 202. One of the finger assemblies 206 that receives a thumb of the use, a thumb assembly 236, adjustably connects to the thumb platform 234. By way of example, the thumb assembly 236 adjustably connects to the thumb platform 234 at different positions to match different thumb lengths, different web sizes between the thumb and an index finger of the user. The thumb assembly 236 includes a thumb rail guide 238, a thumb follower assembly 240 that connects the thumb rail guide 238 to the actuator 208. The thumb rail guide 238 has an arc-shaped thumb rail track 242. Thumb bearings 244 are moveably disposed within the thumb rail track 242 so that the thumb follower assembly 240 follow a path of the thumb rail guide 238 along the thumb rail track 242. A thumb strap holder 254 connects to a bottom side of the thumb rail guide 238 and adjustably fixes a finger strap 250 through a strap position adjustable slot 252 that is disposed within a cavity of the thumb strap holder 254. By way of example, the thumb strap holder 254 is made of a soft pad.

In an example embodiment, the actuator base 210 fixes onto the external platform 202 by, for example a screw set, at one end, and connects to the actuator 208 at the other end via, for example a hinge joint, at the other end. The actuator base 210 facilitates a proper alignment of the actuator 208, such that the actuator 208 and the finger assembly 206 are properly aligned.

In one example embodiment, the side fixation bracket 212 adjustably connects to a little finger side of the external platform 202 at different lateral positions to match different palm sizes.

In an example embodiment, the strain gauge sensor 232 measures a resultant force generated by the finger of the user. By way of example, the resultant force generated has a range of magnitude of 0-50 N.

Figure 3A:
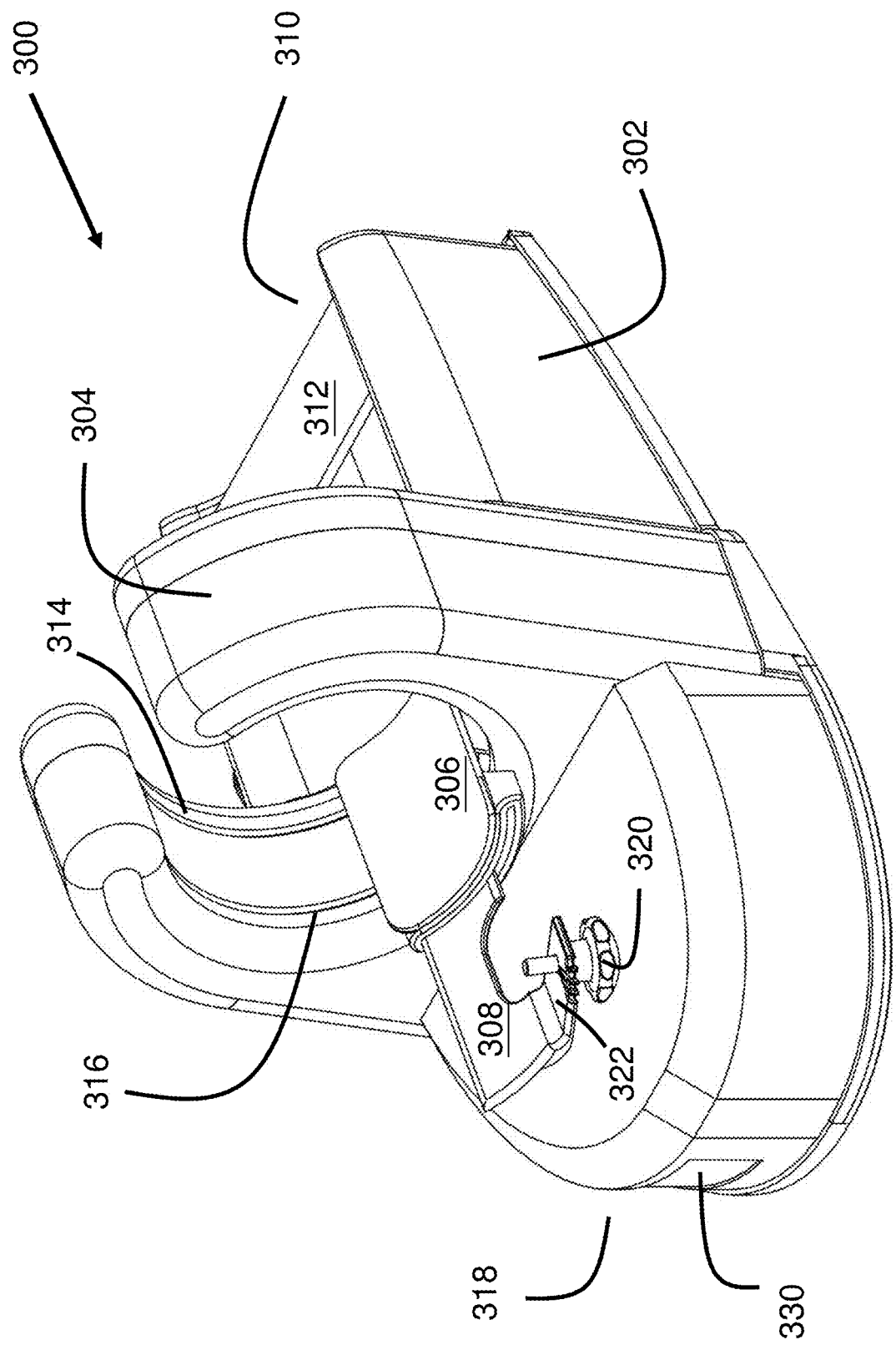
FIG. 3A shows an oblique view of a base in accordance with an example embodiment.
Figure 3B:
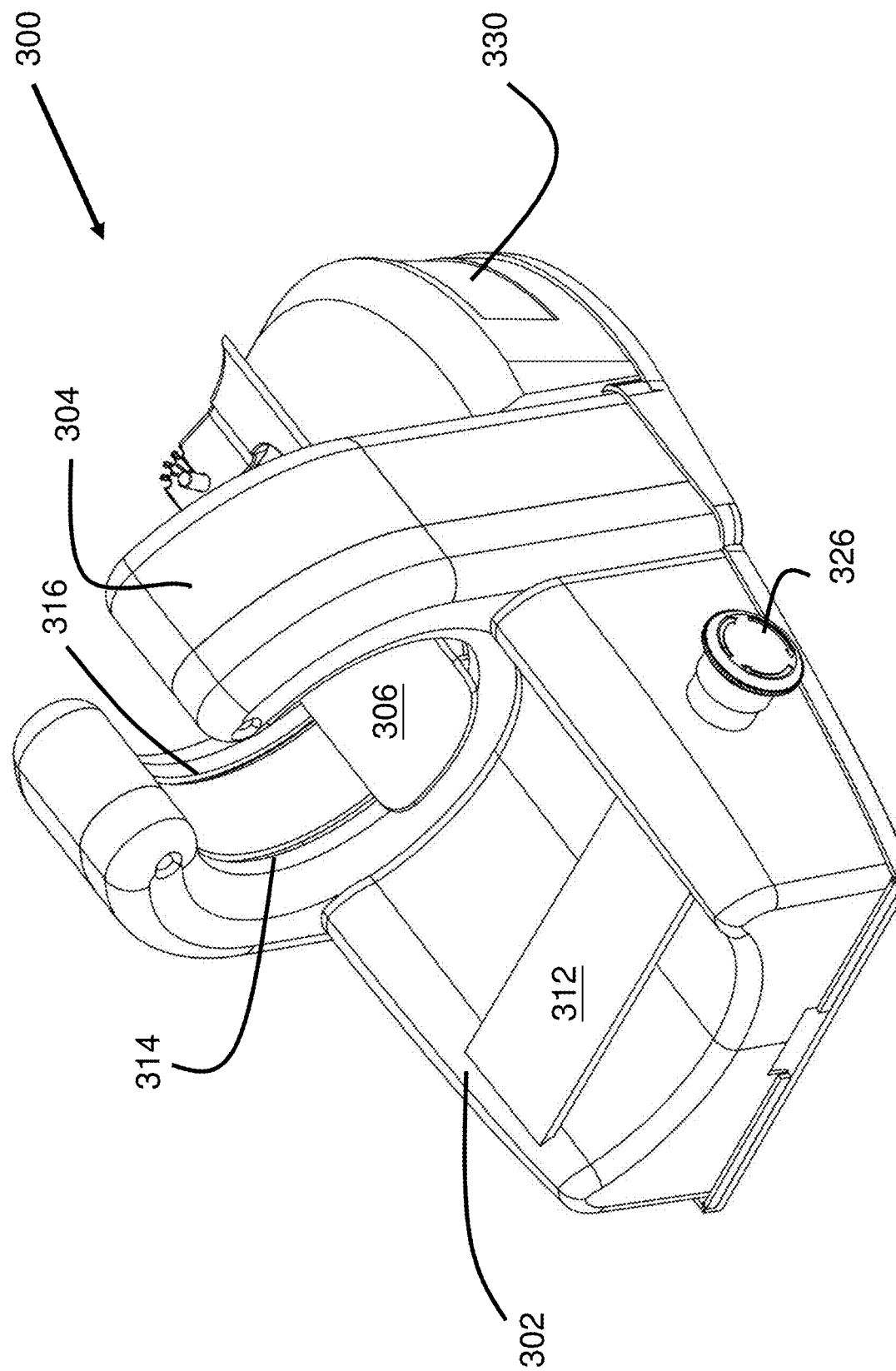
FIG. 3B shows a rear view of a base in accordance with an example embodiment.
Figure 3C:
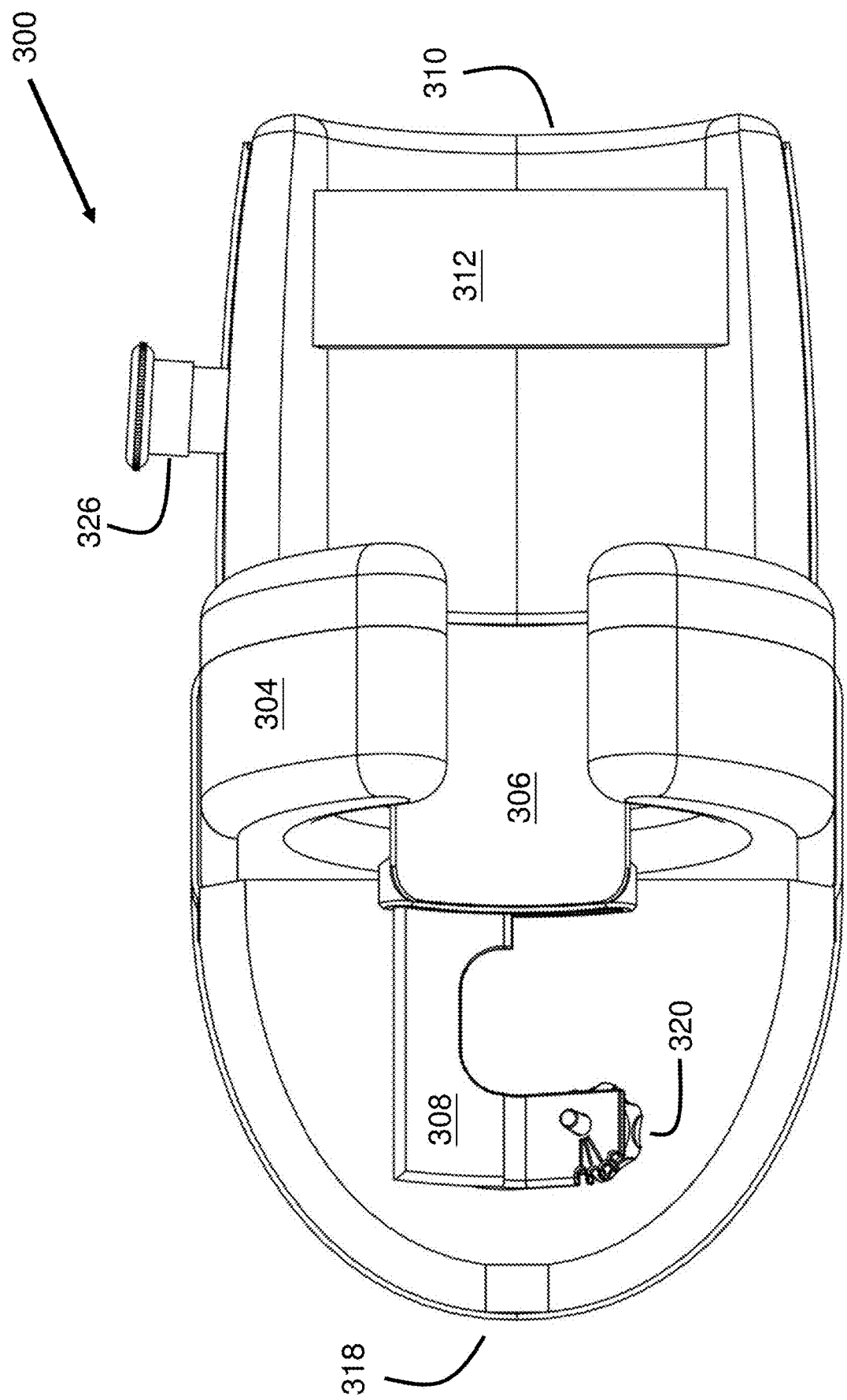
FIG. 3C shows a top view of a base in accordance with an example embodiment.

FIGS. 3A-3C show a base (or a forearm base) 300 of the device in accordance with an example embodiment. The base 300 includes a forearm support 302, a C-shaped ring 304 that abuts the forearm support 302, a rotatable platform 306, and a mounting platform 308.

The forearm support 302 locates at a proximal end 310 of the base 300 and receives a forearm of the user. A forearm strap 312 is adjustably located near an opening of the forearm support 302. Once the forearm of the user is placed on the forearm support 302, the forearm strap 312 can wrap around an upper surface of the forearm so as to secure the forearm onto the forearm support 302.

The C-shaped ring 304 abuts the forearm support 302 and includes a track(s) formed along an inner circumferential surface of the C-shaped ring 304 for the rotatable platform 306 to move therealong. In the example embodiment as shown, the C-shaped ring 304 includes a first C-shaped track 314 and a second C-shaped track 316 that are formed along an inner circumferential surface of the C-shaped ring 304. The rotatable platform 306 moves along the first C-shaped track 314 and the second C-shaped track 316 and receives a forearm of the user. The rotatable platform 306 moves in a clockwise direction to demonstrate a pronation action of the wrist, while an anti-clockwise movement of the rotatable platform 306 demonstrates a supination action of the wrist.

In another example embodiment, the C-shaped ring can have more than two tracks that are formed along the inner circumferential surface of the C-shaped ring for the rotatable platform to move therealong.

In an example embodiment, the rotatable platform 306 moves between a maximum supination position and a maximum pronation position. In one example embodiment, the maximum supination position and the maximum pronation position can be set by the user according to his/her needs. By way of example, the maximum supination position is pre-set at a position 45 degrees clockwise from a neutral position of (i.e. a position where a thumb of the user faces upwards and is regarded as 0 degree), and the maximum pronation position is pre-set at a position 90 degrees anti-clockwise from the neutral position of 0 degree. The rotatable platform 306 supinates (i.e. moves in a clockwise direction for a right hand) from a neutral position (i.e. 0 degree) up to 45 degrees with respect to the neutral position of the base 300 at the maximum supination position. The rotatable platform 306 pronates (i.e. moves in an anti-clockwise direction for a right hand) from the neutral position up to 90 degrees with respect to the neutral position of the base 300 at the maximum pronation position. In other words, the rotatable platform 306 can move clockwise from 0 to 90 degrees to demonstrate pronation of the wrist between 0 and 90 degrees, and can move anti-clockwise from 0 to 45 degrees to demonstrate supination of the wrist between 0 and 45 degrees.

The mounting platform 308 connects to and extends from a distal end 318 of the rotatable platform 306 and removably mounts a hand brace onto the base 300. By way of example, the mounting platform 308 is an L-shaped plate. A locking knob 320 removably connects to and securely locks at the mounting platform 308 at an extended end 322 of the mounting platform 308. By way of example, the locking knob 320 inserts into a hole on the extended end 322 of the mounting platform 308 to removably connect to the mounting platform 308.

In another example embodiment, the locking knob can have threads that match internal threads on a hole of the mounting platform, so that the locking knob can screwably connect to and securely locks at the mounting platform.

In an example embodiment, there are two interchangeable mounting platforms with two differently oriented mounting parts that mount the hand brace onto the base for left and right hands respectively.

The locking knob 320 adjustably mounts a hand brace of the device onto the mounting platform 308 and fixes a wrist of the user at different positions when the user is undergoing a training of finger extension and finger flexion. By way of example, the locking knob 320 fixes the wrist at three different wrist positions. When the wrist is fixed at a first wrist extension position, the wrist rests at a neutral position of 0 degree with respect to a longitudinal axis of a forearm of the user. When the wrist is fixed at a second wrist extension position, the wrist extends 15 degrees with respect to the longitudinal axis of the forearm. When the wrist is fixed at a third wrist extension position, the wrist extends 30 degrees with respect to the longitudinal axis of the forearm.

In one example embodiment, the emergency stop button 326 is provided on a side of the base 300 and enables the user to stop the base 300 from operation to protect the user in case any unexpected malfunction of any part of the base 300.

In an example embodiment, a rechargeable battery 330 is removably provided on the distal end 318 of the base 300. By way of example, upon a full recharge, the rechargeable battery 330 enables the base 300 to run for four hours continuously. By way of example, the rechargeable battery is a lithium-polymer battery.

Figure 3D:
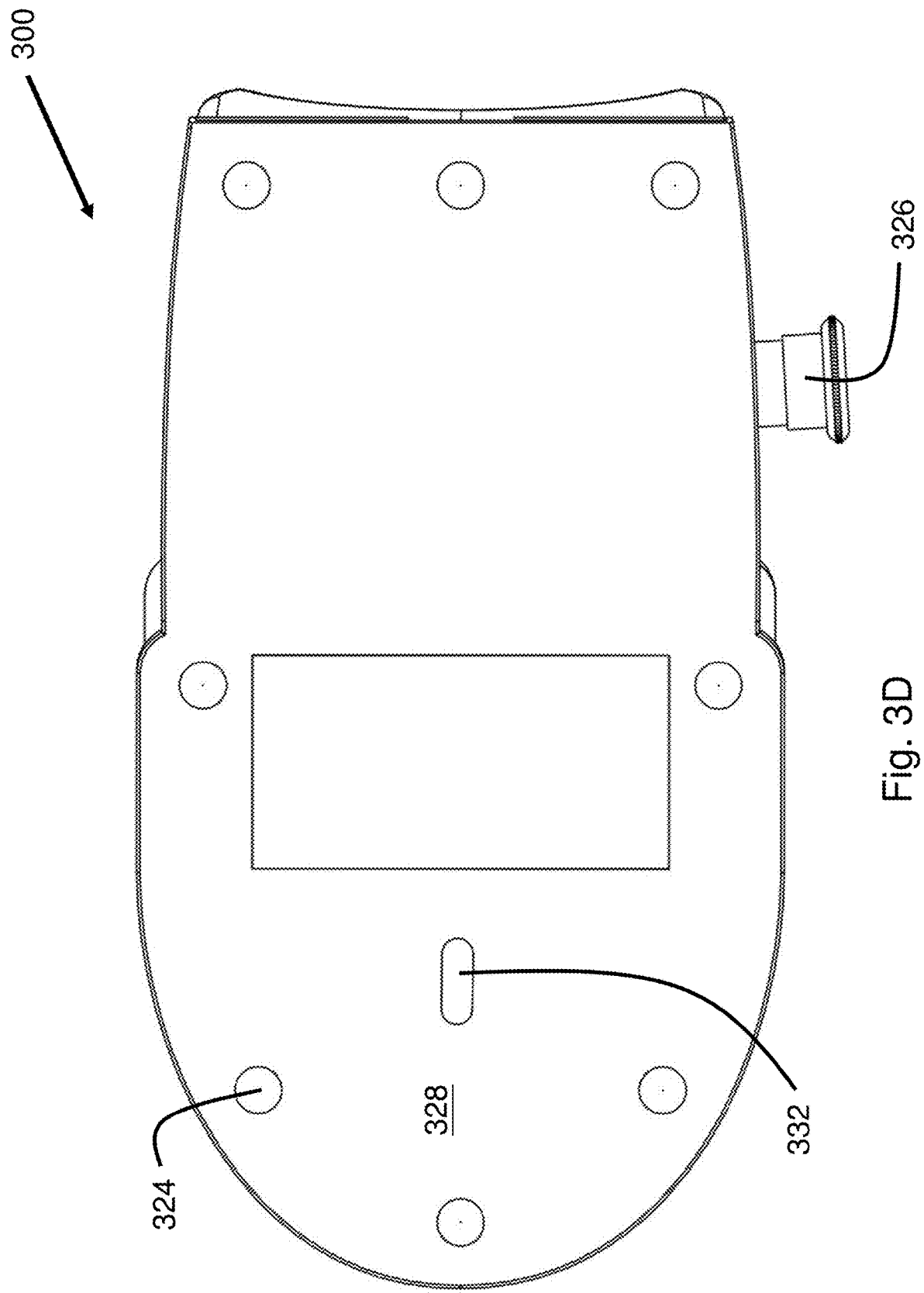
FIG. 3D shows a bottom view of a base in accordance with an example embodiment.

FIG. 3D shows a bottom plate 328 of the base 300. In the example embodiment as shown, a plurality of bearing rollers 324 and a position tracking sensor 332 are provided on the bottom plate 328 of the base 300. By way of example, there are eight bearing rollers provided on the bottom part of the base. Bearing rollers 324 allow the base 300 to move smoothly on a surface where the base 300 sits on. The position tracking sensor 332 tracks a route of movement of the user on using the base 300. By way of example, the position tracking sensor 332 is a complementary metal oxide semiconductor (CMOS) sensor for position tracking so that the user is able to move over an area on using the base 300.

Referring back to FIG. 1A, flexion and extension of the fingers are exercised through the actions of finger assemblies 106 of the hand brace 102, while supination and pronation of the forearm are exercised through the rotational movement of a rotatable platform 108 along an inner circumferential surface of a C-shaped ring 110 of the base 104. In one example embodiment, the power assistive device 100 includes an actuator positioning controller that controls a speed of supination and pronation (i.e. a speed of the rotatable platform), so that a cycle time of supination/pronation is the same as a cycle time of flexion/extension to achieve synchronization between the finger assemblies 106 and the rotatable platform 108.

In an example embodiment, when there is difficulty for the finger assemblies 106 to move smoothly, for example due to a blockage to the finger assemblies, the action of flexion or extension will stop and the finger assemblies will return to an opposite direction in order to avoid any damages to the user and to the device 100.

In another embodiment, as a safety feature, a next cycle of finger flexion/extension and forearm supination/pronation will not start until both movements of the finger flexion/extension and forearm supination/pronation have completed. As such, synchronization between the finger assemblies 106 and the rotatable platform 108 can be attained and no time shift between the two movements of the finger flexion/extension and forearm supination/pronation after several cycles can be ensured.

Figure 4A:
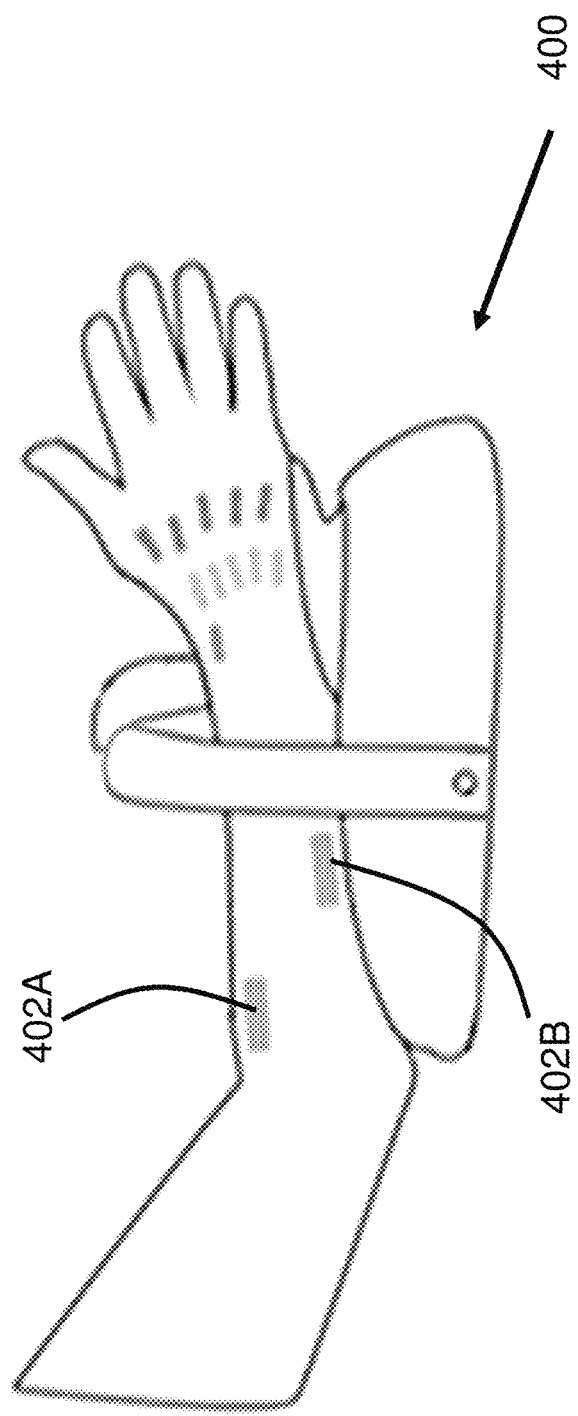
FIG. 4A shows a side view of a hand wearing a power assistive device in accordance with an example embodiment.

FIG. 4A shows a user that wears the power assistive device 400 in the hand rehabilitation system in accordance with an example embodiment. Two electromyography (EMG) sensors 402A 402B removably attach to a forearm of the user. By way of example, the EMG sensor 402A removably attaches to a flexor digitorum muscle and EMG sensor 402B removably attaches to an extensor digitorum muscle.

Figure 4B:
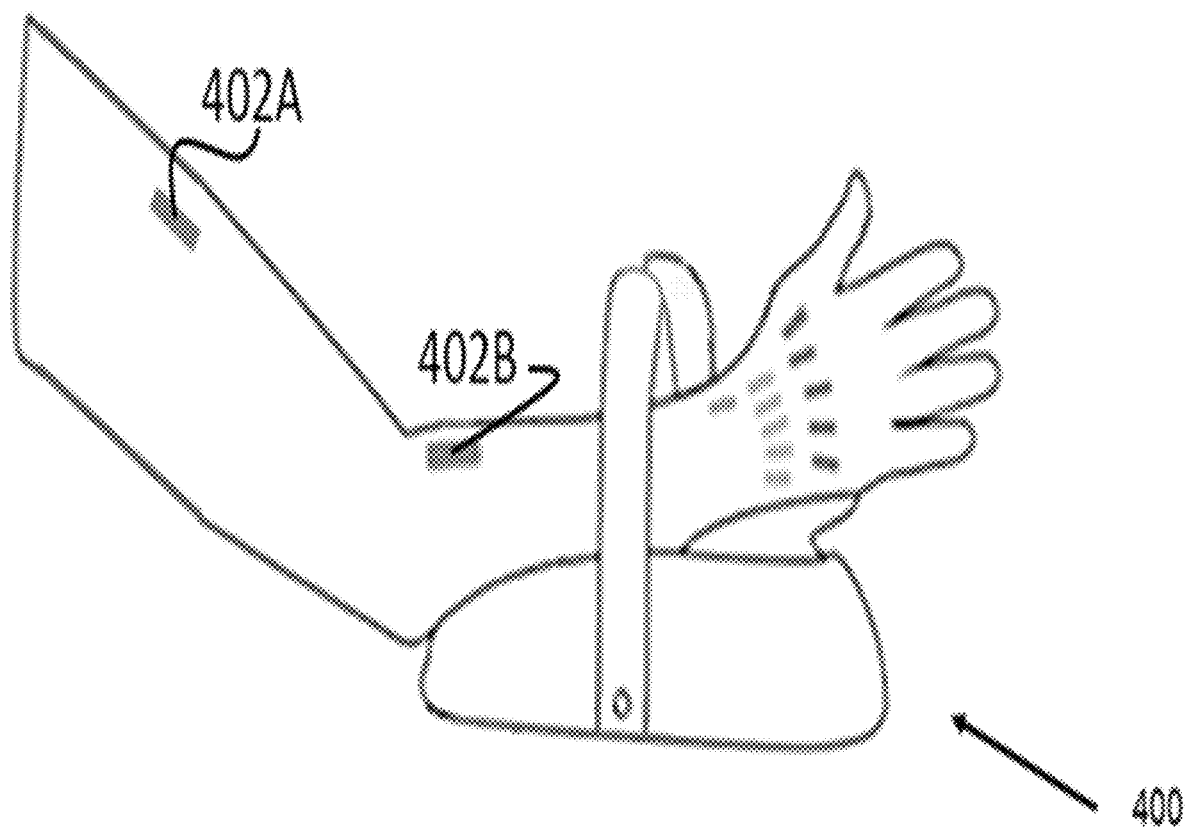
FIG. 4B shows a side view of a hand wearing a power assistive device in accordance with an example embodiment.

FIG. 4B shows a user that wears the power assistive device 400 in the hand rehabilitation system in accordance with another example embodiment. An electromyography (EMG) sensor 402A attaches to an upper arm of the user while 402B sensor attaches to a forearm of the user. By way of example, the EMG sensor 402A removably attaches to a Biceps Brachii muscle and EMG sensor 402B removably attaches to either flexor digitorum, extensor digitorum or pronator teres muscle in the forearm.

In an example embodiment, each of the EMG sensors 402A and 402B includes two EMG electrodes that are opposite in polarity. By way of example, the two EMG electrodes sense either finger flexion or finger extension if they are located on the forearm or if they belong to the EMG sensor 402A or the EMG sensor 402B. By way of example, the two EMG electrodes sense either forearm supination or forearm pronation if one of them is located on the upper arm and other one is located on the forearm, or if they belong to the EMG sensor 402A or the EMG sensor 402B. In other words, the two electrodes of the EMG sensor 402A do not detect different motions of the hand, and the two electrodes of the EMG sensor 402B do not detect different motions of the hand.

In one example embodiment, the EMG sensors are electromyography-mechanomyography (EMG-MMG) sensors that include two EMG electrodes and a MMG sensor. The two EMG electrodes are separate from each other by 20 millimeters (mm) and sense EMG signals. The MMG sensor is located between the two EMG electrodes and senses MMG signals. By way of example, one of the EMG electrodes senses EMG signals for finger flexion and the other EMG electrode senses EMG signals for finger extension. By way of example, one of the EMG electrodes senses EMG signals for forearm supination and the other EMG electrode senses EMG signal for forearm pronation. By way of example, the MMG sensor includes two MMG electrodes in which one of the MMG electrodes senses MMG signals for finger flexion and the other MMG electrode senses MMG signals for finger extension. By way of example, one of the MMG sensor includes two MMG electrodes in which one of the MMG electrodes senses MMG signals for forearm supination and the other MMG electrode senses MMG signals for forearm pronation.

In one example embodiment, a reference electrode can be mounted over an elbow of the user and provides a common reference to inputs of the two EMG electrodes.

The EMG sensors 402A 402B detect EMG signals generated by movement of a hand of the user. EMG signals from an affected muscle of a limb correspond to an intention of the user and can control an assistive motion provided by the power assistive device 400 in the hand rehabilitation system. As such, the user can actively participate in a training of a combined movement of finger flexion-extension and forearm supination-pronation. By way of example, the user can maintain finger flexion/extension while he supinates/pronates his forearm in the same training. If the user can maintain finger extension while supinating, flexor or spastic pattern is improved.

In one example embodiment, the EMG sensors are EMG-MMG sensors that also detect MMG signals generated by movement of a hand of the user.

In one example embodiment, in a training session(s), the actions of finger flexion, finger extension, forearm supination and forearm pronation can be combined in any forms and in any consequences per a demand and a need of the user.

Figure 5:
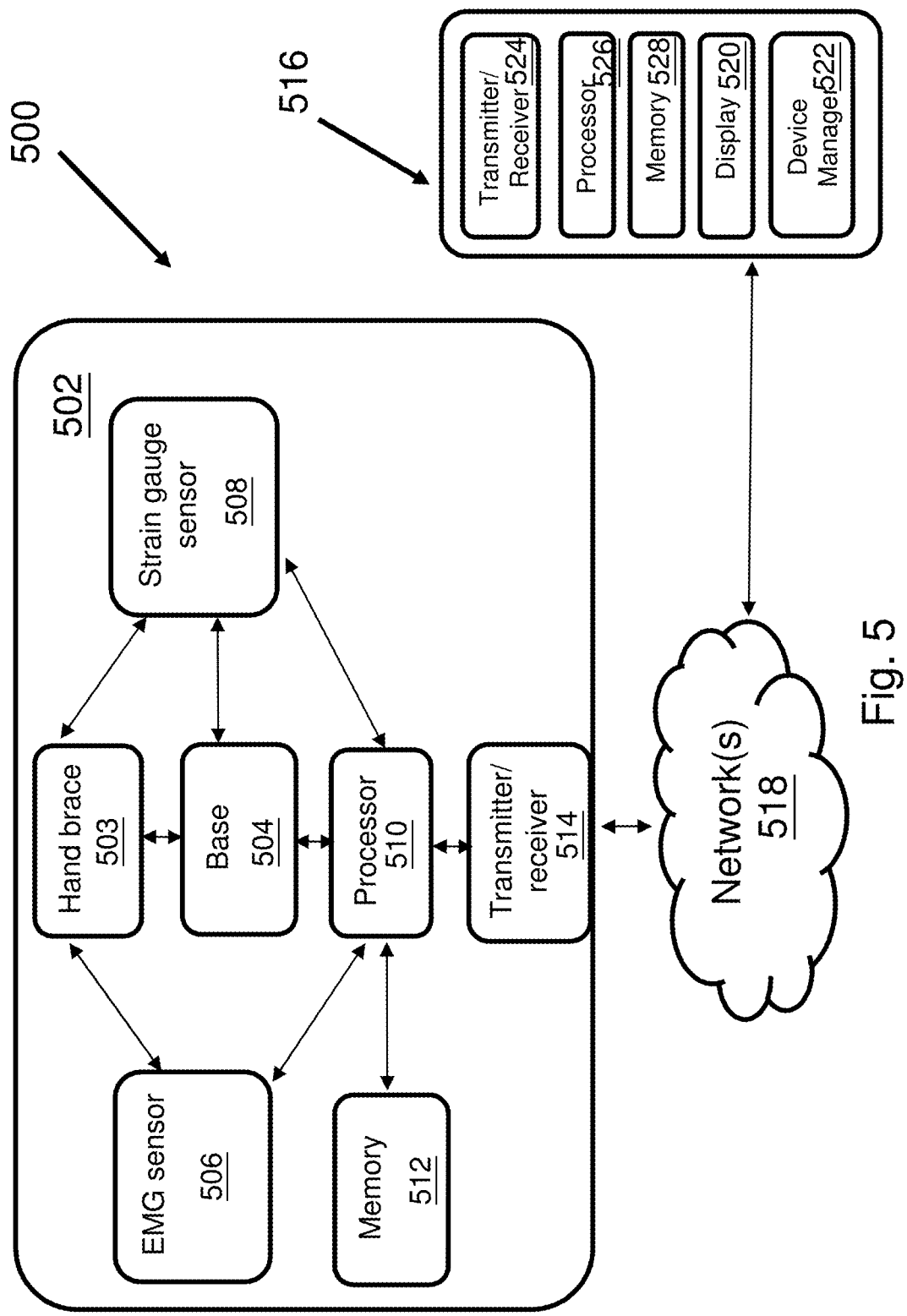
FIG. 5 shows an electronic system that includes a power assistive device in accordance with an example embodiment.

FIG. 5 shows an electronic system 500 that includes the device 502 that communicates with a handheld portable electronic device (HPED) 516 via one or more network(s) 518 accordance with an example embodiment. The device 502 includes a hand brace 503 that removably connects to a base 504, an EMG sensor 506, a strain gauge sensor 508, a processor 510, a memory 512, and a transmitter/receiver 514. The processor 510 communicates with the hand brace 503 and the base 504, and receives EMG signals from the EMG sensor 506, and receives force signals from the strain gauge sensor 508. In an example embodiment, the EMG signals and the force signals are transmitted to the processor 510 in real time during training. The processor 510 analyzes the EMG signals and the force signals to determine an onset time of muscle dynamics of a hand of the user. The processor 510 also communicates with the memory 512 and the transmitter/receiver 514. In one example embodiment, the memory 512 stores the EMG signals the force signals, and the onset time of muscle dynamics, and records movement histories of the hand brace 503 and the base 504.

In one example embodiment, the EMG sensor is an EMG-MMG sensor that senses both EMG signals and MMG signals. The EMG signals, the MMG signals and the force signals are transmitted to the processor in real time during training. The processor analyzes the EMG signals, the MMG signals and the force signals to determine an onset time of muscle dynamics of a hand of the user. The memory stores the EMG signals, the MMG signals, the force signals, and the onset time of muscle dynamics, and records movement histories of the hand brace and the base.

The transmitter/receiver 514 wirelessly receives commands from the HPED 516 to operate the device 502 for providing training of a combined movement of finger flexion-extension and forearm supination-pronation to the user. By way of example, the transmitter/receiver 514 receives commands form the HPED to actuate finger assemblies of the hand brace 503 to provide a training of finger flexion and finger extension to the user. By way of example, the transmitter/receiver 514 receives commands form the HPED to move a rotatable platform of the base 504 to provide a training of forearm supination and forearm pronation to the user. In one example embodiment, the rotatable platform moves along C-shaped tracks of the base 504.

The HPED 516 (such as a smartphone, a tablet computer, a laptop, or other computer) can include a memory 528, a display 520, a device manager 522, a transmitter/receiver 524, and a processor 526. The memory 518 stores the information transmitted from the device 502. In an example embodiment, the information includes the EMG signals, the MMG signals, the force signals, the onset time of muscle dynamics, and a profile of the user. The display 520 displays the information and the device manager 522 (such as a software application) enables the user to communicate with the device 502, such as making commands to provide a training of finger flexion-extension and/or a training of forearm supination-pronation to the user. The transmitter/receiver 524 wirelessly transmits commands from the HPED to the device 502, and receives information stored in the memory 512 of the device 502.

Figure 6:
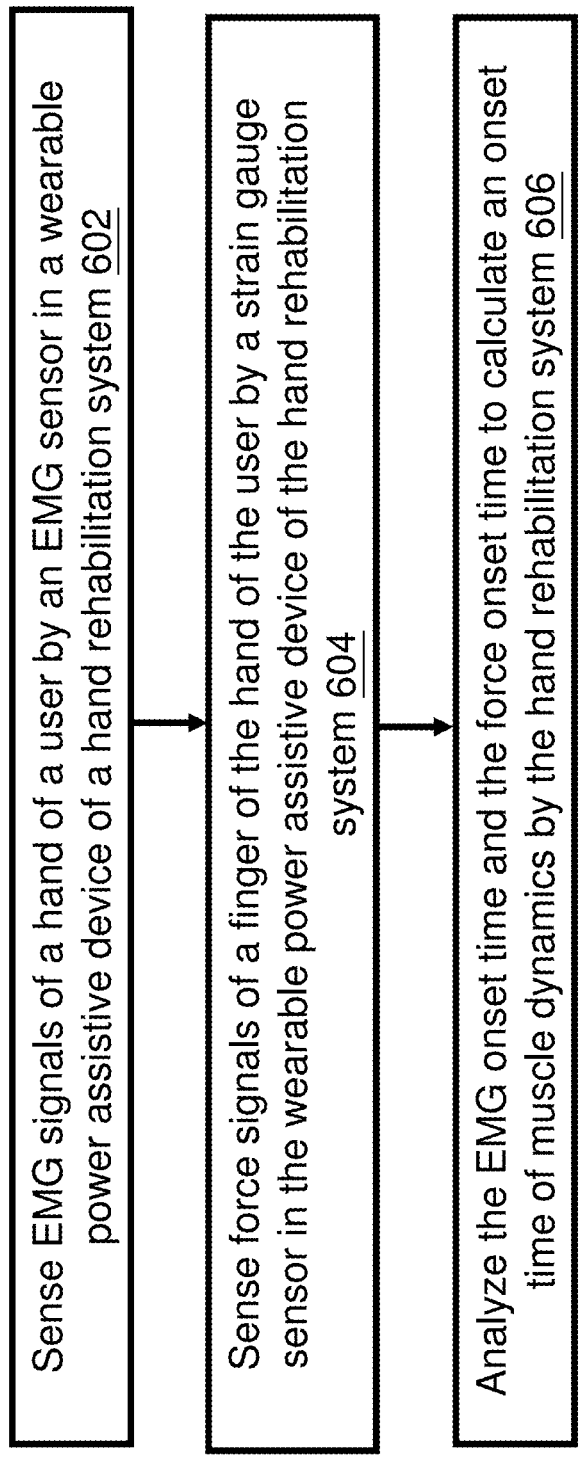
FIG. 6 shows a method executed by a hand rehabilitation system to determine an onset time of muscle dynamics in accordance with an example embodiment.

FIG. 6 shows a method executed by a hand rehabilitation system to determine an onset time of muscle dynamics. Electromyography (EMG) signals of a hand of a user are sensed by an EMG sensor in a power assistive device in the hand rehabilitation system in box 602. Force signals of a finger of the hand of the user are sensed by a strain gauge sensor in the power assistive device in the hand rehabilitation system in box 604. The hand rehabilitation system calculates an EMG onset time from the EMG signals and a force onset time from the force signals in box 606. The hand rehabilitation system analyzes the EMG onset time, and the force onset time to calculate the onset time of muscle dynamics in box 608.

In one example embodiment, mechanomyography (MMG) signals of the hand of the user are sensed by an MMG sensor in the power assistive device in the hand rehabilitation system. The hand rehabilitation system calculates an EMG onset time from the EMG signals, an MMG onset time from the MMG signals, and a force onset time from the force signals. The hand rehabilitation system analyzes the EMG onset time, the MMG onset time, and the force onset time to calculate the onset time of muscle dynamics.

Figure 7:
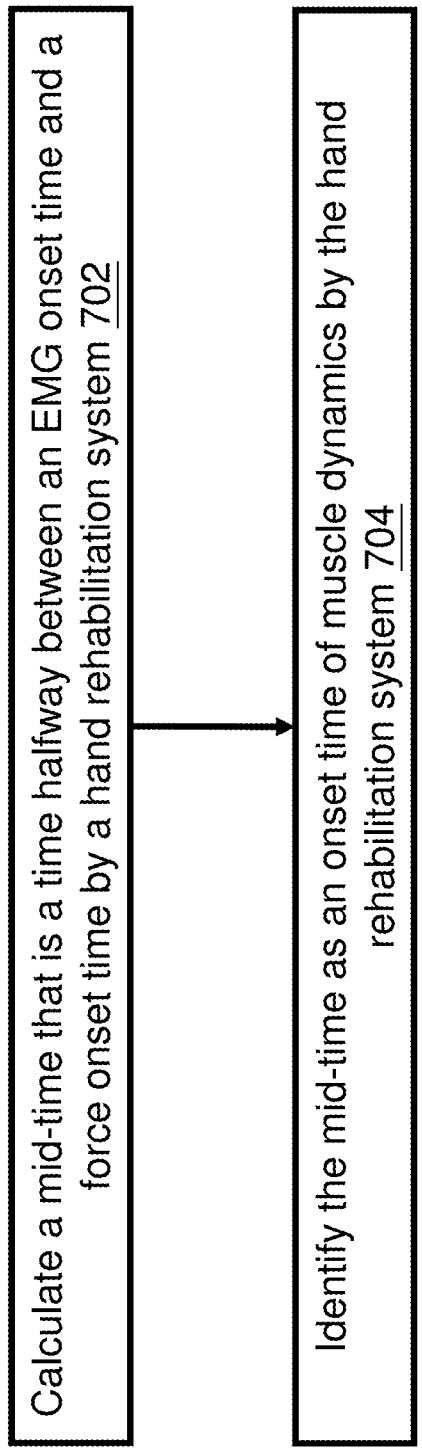
FIG. 7 shows a method executed by a hand rehabilitation system to calculate an onset time of muscle dynamics in a hand rehabilitation system.

FIG. 7 shows a method to calculate an onset time of muscle dynamics in a hand rehabilitation system. A mid-time that is a time halfway between an EMG onset time and a force onset time is calculated by the hand rehabilitation system in box 702. The mid-time is identified as the onset time of muscle dynamics in box 704.

In one example embodiment of a method to calculate an onset time of muscle dynamics in a hand rehabilitation system, a first average value between an EMG onset time and a force onset time is calculated by the hand rehabilitation system. A second average value between an MMG onset time and the force onset time is calculated by the hand rehabilitation system. The first average value is determined, by the hand rehabilitation system, to be the onset time of muscle dynamics if a first EMG signal is sensed earlier than a first MMG signal. The second average value is determined, by the hand rehabilitation system, to be the onset time of muscle dynamics if the first MMG signal is sensed earlier than the first EMG signal.

Figure 8:
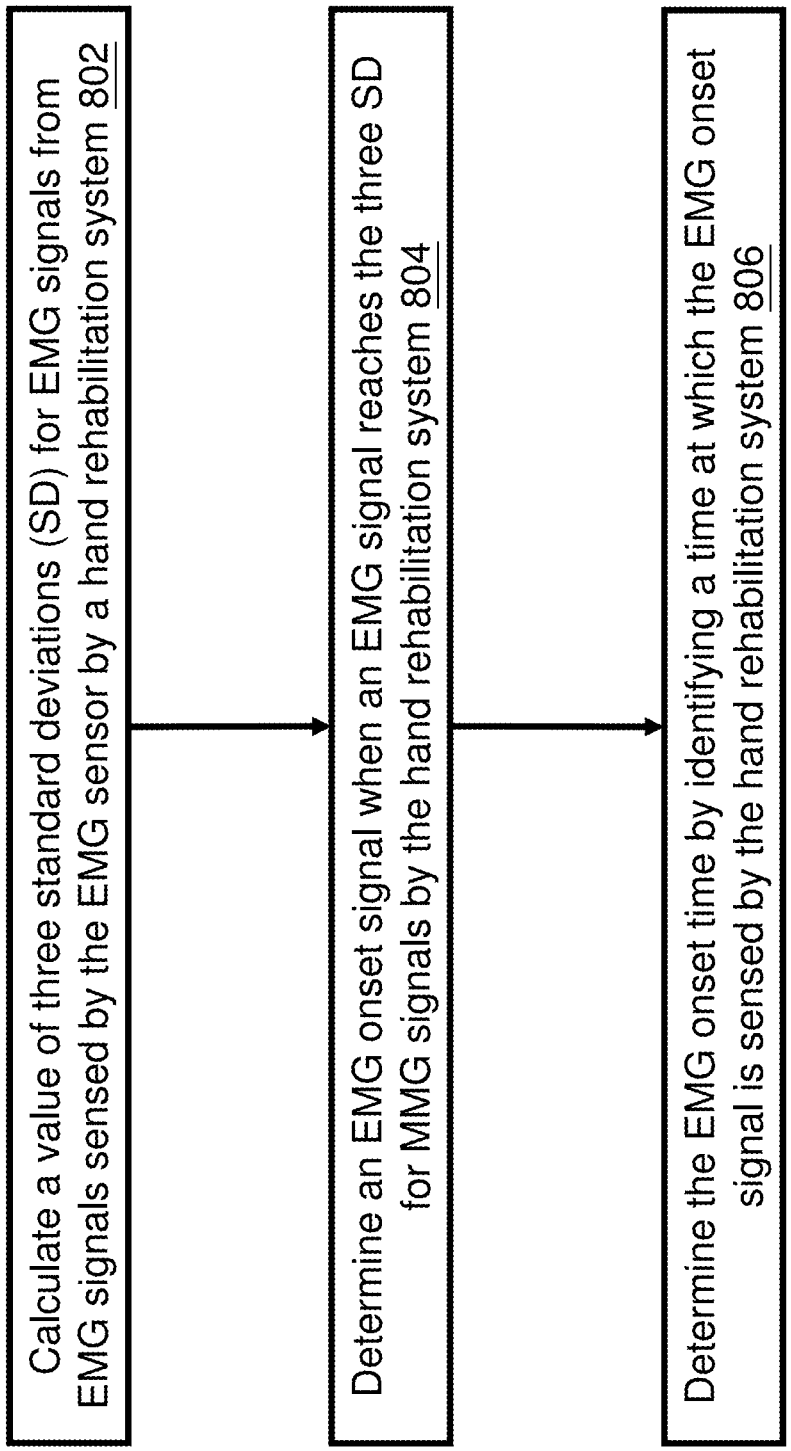
FIG. 8 shows a method executed by a hand rehabilitation system to determine an EMG onset time of muscle dynamics in accordance with an example embodiment.

FIG. 8 shows a method to determine an EMG onset time in a hand rehabilitation system. The hand rehabilitation system calculates a value of three standard deviations (SD) for EMG signals from the EMG signals sensed by an EMG sensor in box 802. The hand rehabilitation system determines an EMG onset signal when an EMG signal reaches the three SD for EMG signals in box 804. The hand rehabilitation system determines the EMG onset time by identifying a time at which the EMG onset signal is sensed in box 806.

Figure 9:
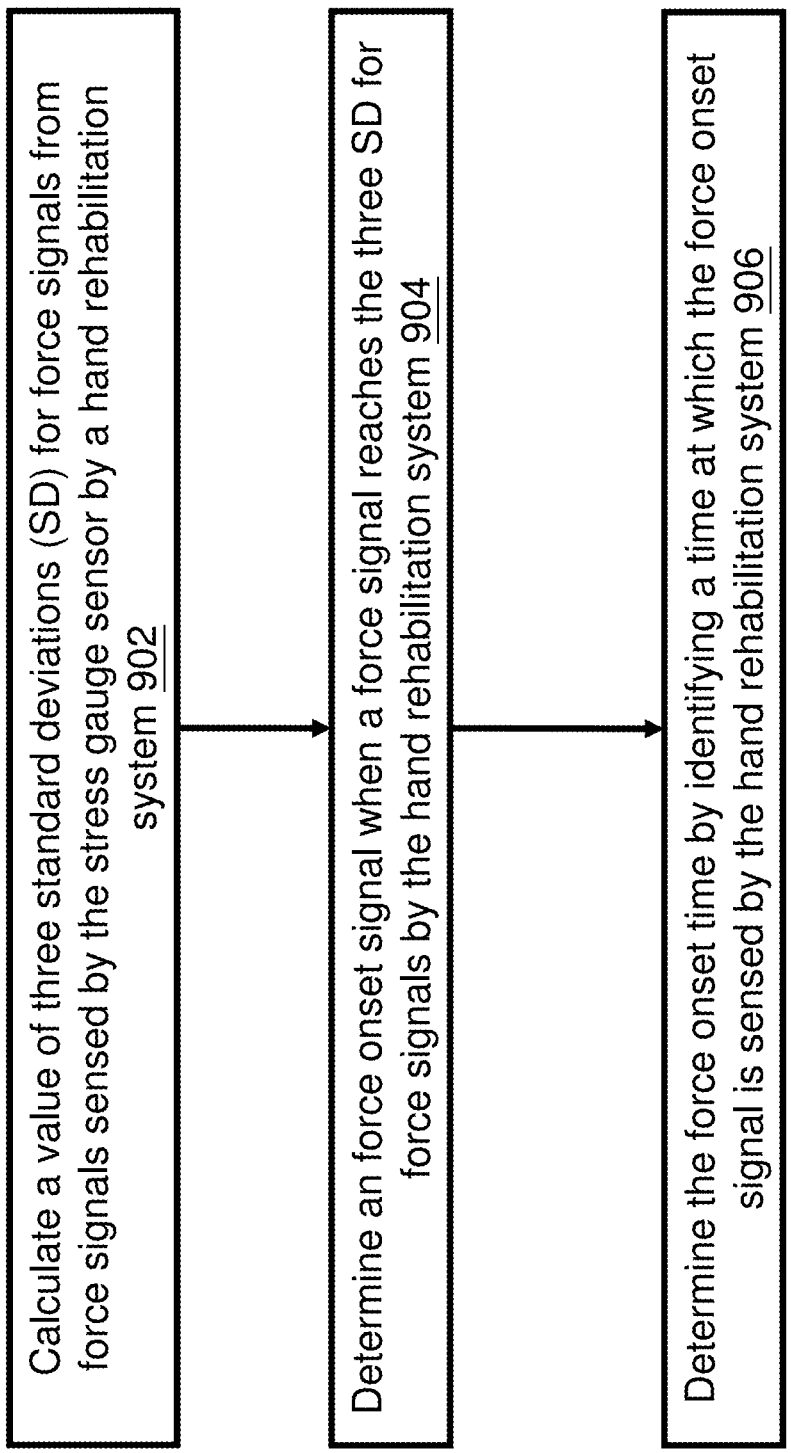
FIG. 9 shows a method executed by a hand rehabilitation system to determine a force onset time of muscle dynamics in accordance with an example embodiment.
Figure 10A:
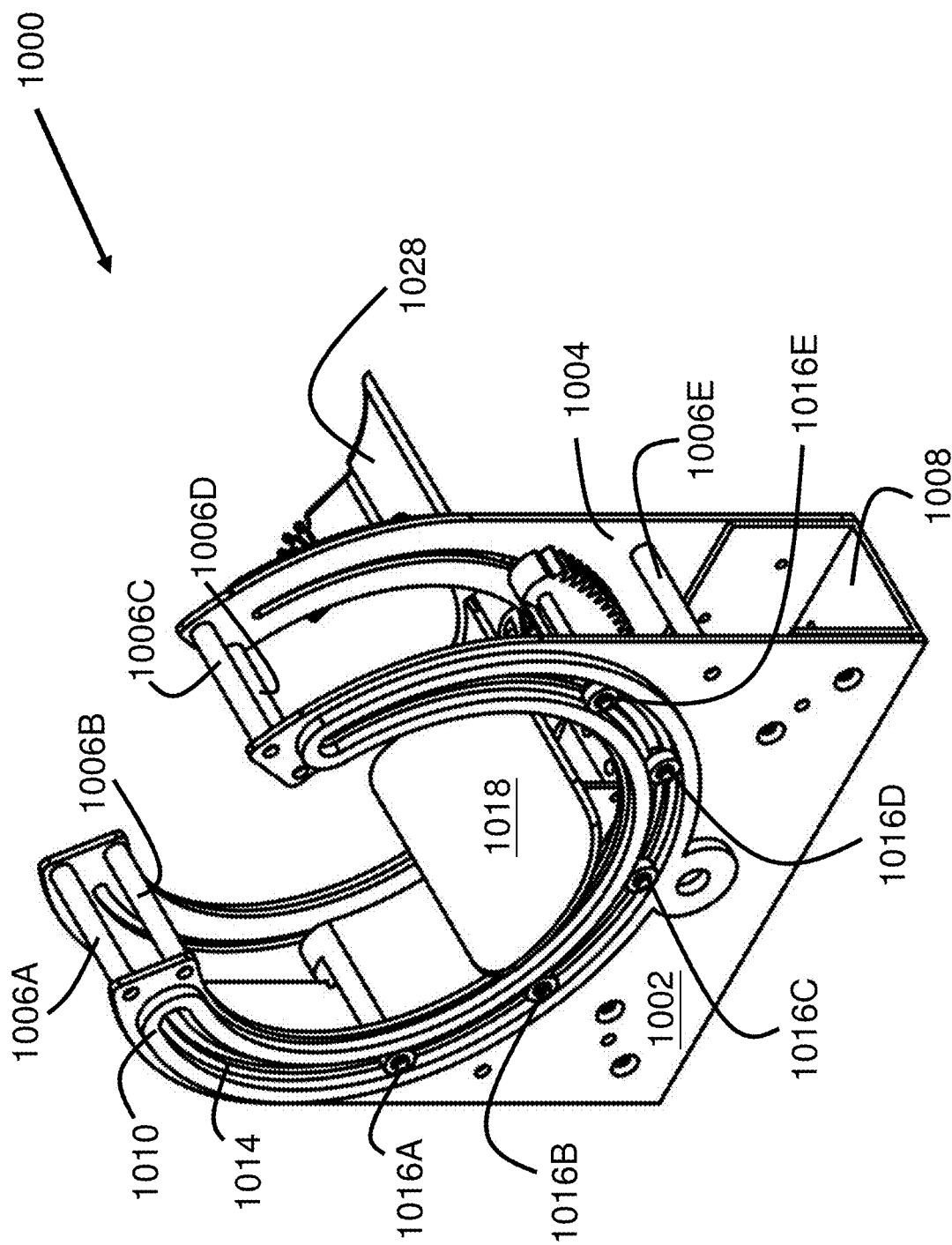
FIG. 10A shows an oblique view of a C-shaped ring in accordance with an example embodiment.
Figure 10B:
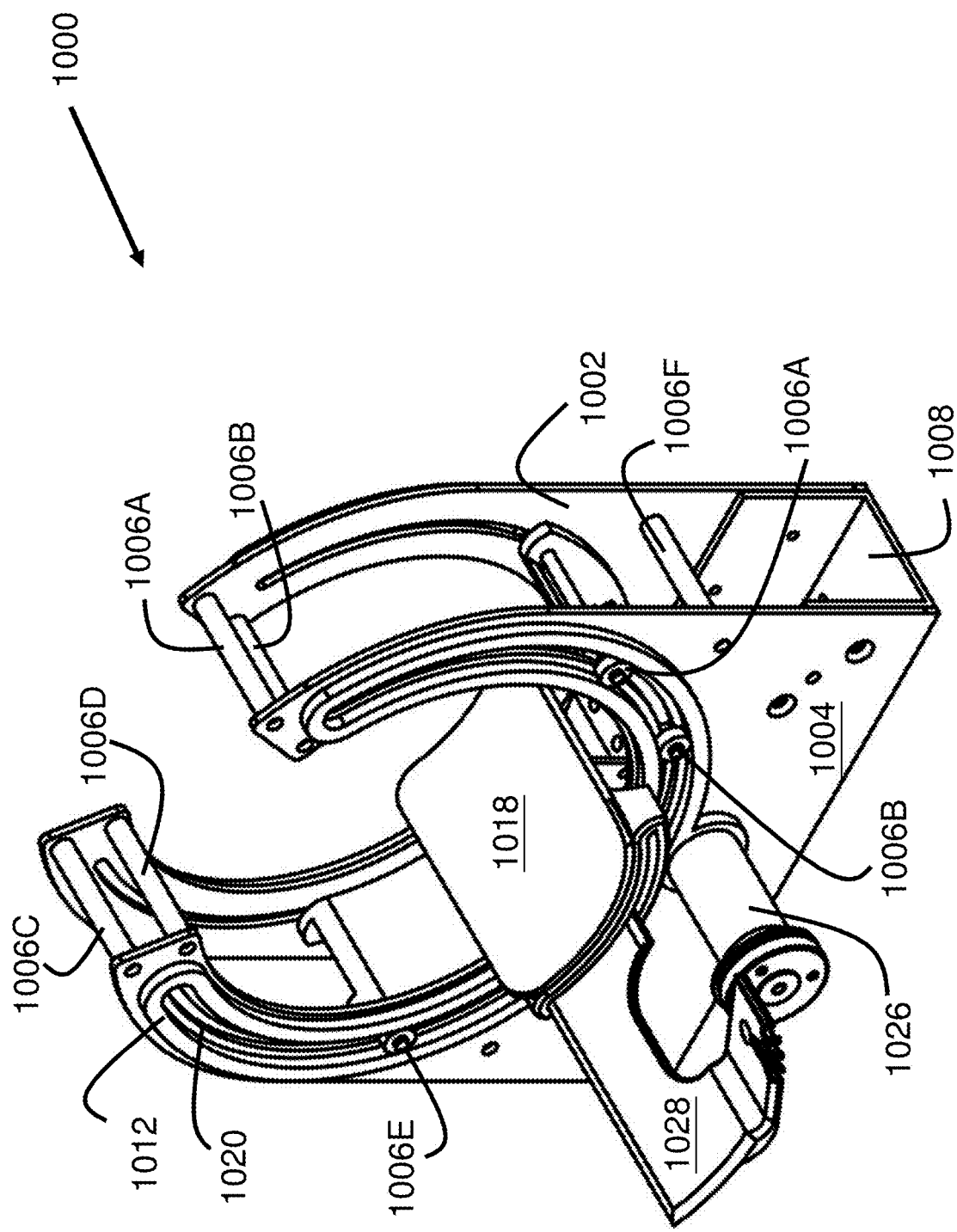
FIG. 10B shows a rear view of a C-shaped ring in accordance with an example embodiment.
Figure 10C:
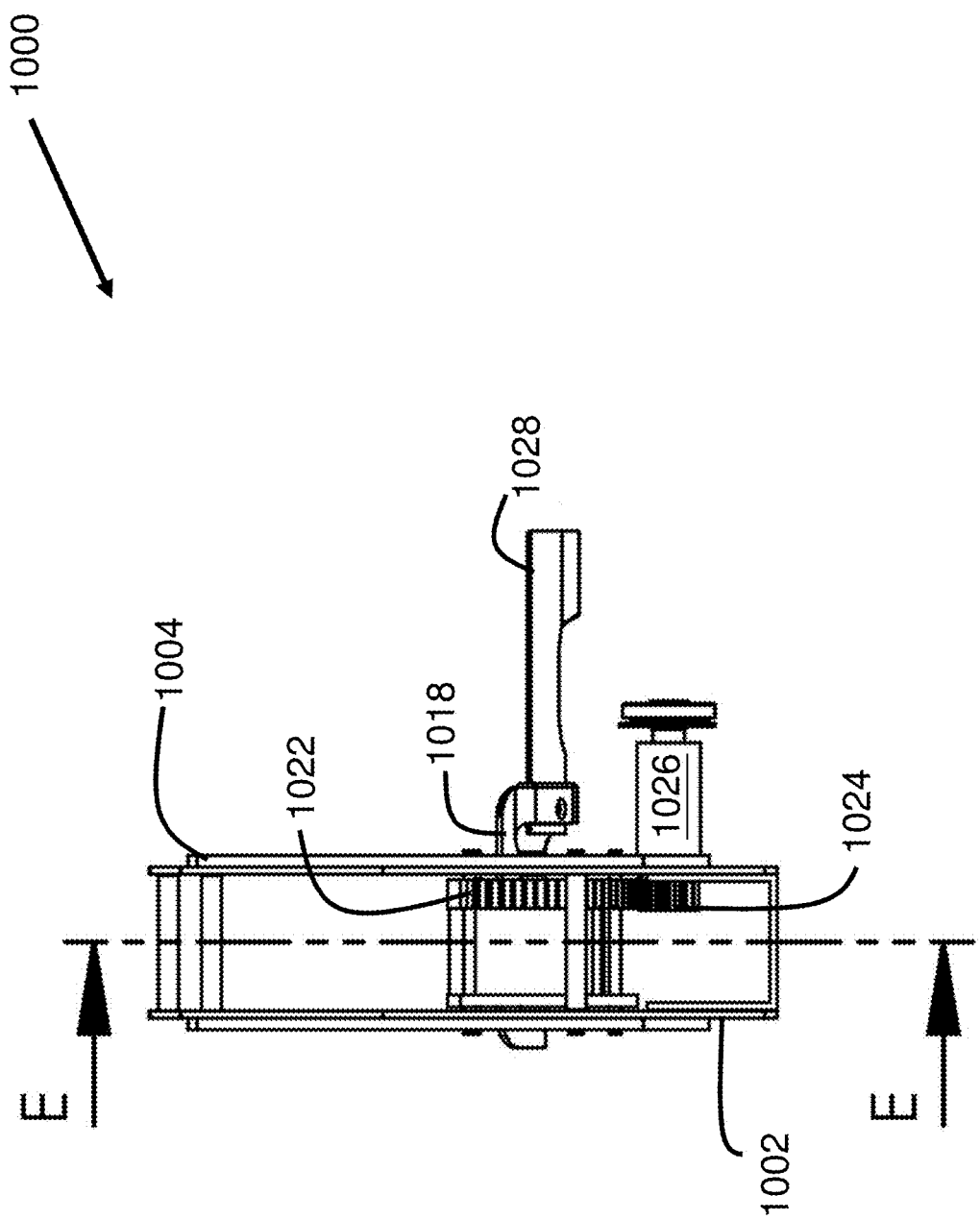
FIG. 10C shows a side view of a C-shaped ring in accordance with an example embodiment.
Figure 10D:
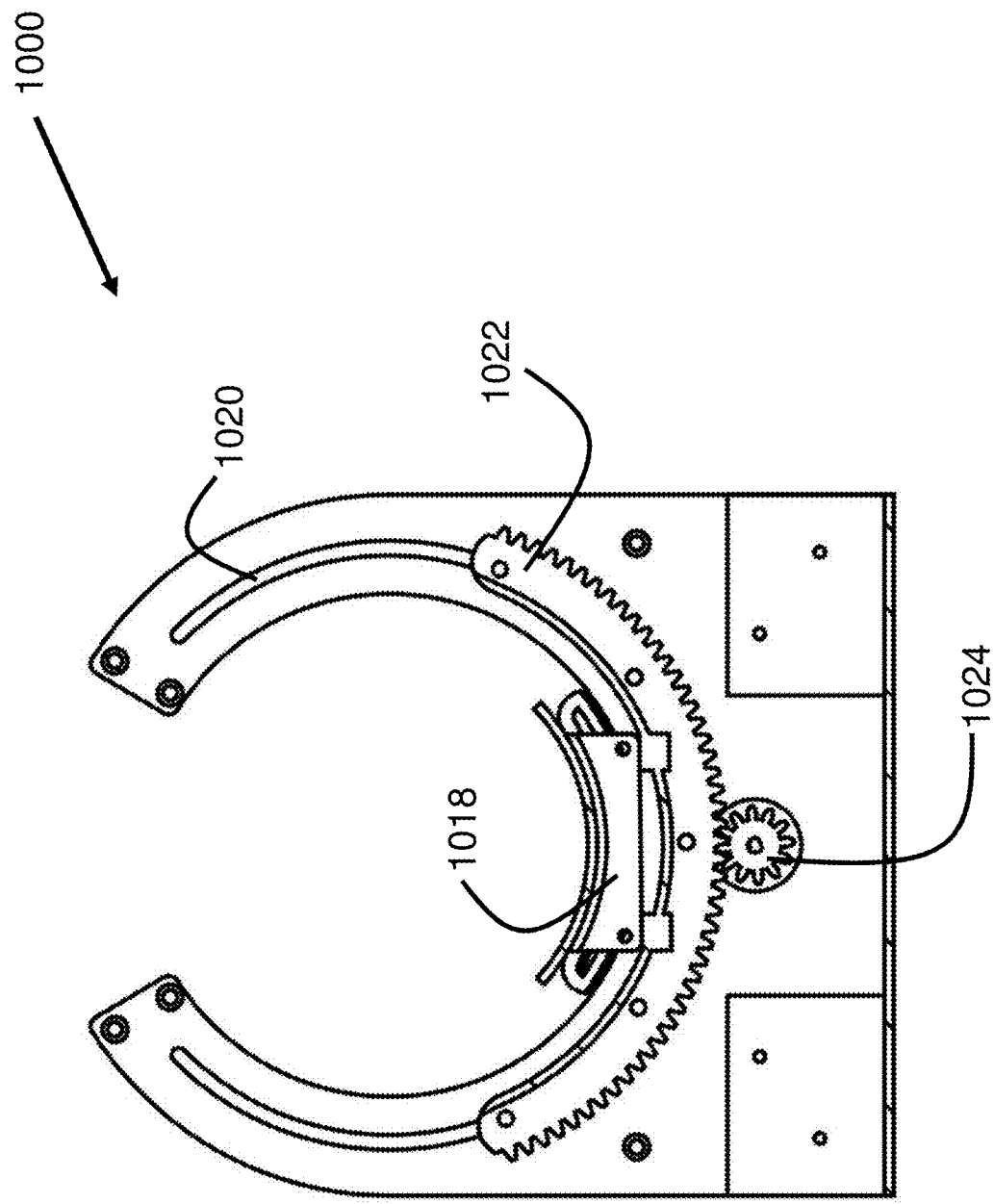
FIG. 10D shows a cross-sectional view of a C-shaped ring along an E-E line of FIG. 10C in accordance with an example embodiment.

FIG. 9 shows a method to determine a force onset time in a hand rehabilitation system. The hand rehabilitation system calculates a value of three standard deviations (SD) for force signals from the force signals sensed by a strain gauge sensor in box 902. The hand rehabilitation system determines a force onset signal when a force signal reaches the three SD for force signals in box 904. The hand rehabilitation system determines the force onset time by identifying a time at which the force onset signal is sensed in box 906.

In an example embodiment, a method to determine an MMG onset time in a hand rehabilitation system is provided. The hand rehabilitation system calculates a value of three standard deviations (SD) for MMG signals from the MMG signals sensed by an MMG sensor. The hand rehabilitation system determines an MMG onset signal when a MMG signal reaches the three SD for MMG signals. The hand rehabilitation system determines the MMG onset time by identifying a time at which the MMG onset signal is sensed.

FIGS. 10A to 10D show an internal structure of a C-shaped ring 1000 in accordance with an example embodiment. The C-shaped ring 1000 includes a front plate 1002 and a back plate 1004 connects to the front plate 1002 through connecting rods 1006A-1006F and a U-shaped connecting plate 1008. A first C-shaped track 1010 is disposed on the front plate 1002 and includes a first rotary track 1014. A second C-shaped track 1012 is disposed on the back plate 1004 and includes a second rotary track 1020. Rotary bearings 1016A to 1016E are movably disposed within the first rotary track 1014 and the second rotary track 1020 to facilitate a rotational movement of a rotatable platform 1018 along the two rotary tracks 1014 and 1020. A forearm of the user rests on and secures onto the rotatable platform 1018 by, for example, a strap wrapping around the forearm so that the forearm rotates with the rotatable platform 1018. In an example embodiment, the rotatable platform 1018 moves in a clockwise direction to demonstrate a supination action of the wrist of a right hand, while an anti-clockwise movement of the rotatable platform 1018 demonstrates a pronation action of the wrist of the right hand. A mounting platform 1028 connects to a distal end of the rotatable platform 1018.

In one example embodiment, the bearings 1016A to 1016E connect to a spur-shaped gear ring 1022 and the gear ring 1022 engages with a motor gear 1024. During operation, a motor 1026 drives the motor gear 1024 to rotate in which teeth of the motor gear 1024 engages with teeth of the gear ring 1022 to drive a rotational movement of the gear ring 1022, the bearings 1016A to 1016E, and the rotatable platform 1018 along the two rotary tracks 1014 and 1020. The forearm of the user rotates as a result of the rotational movement of the rotatable platform 1018.

Figure 11A:
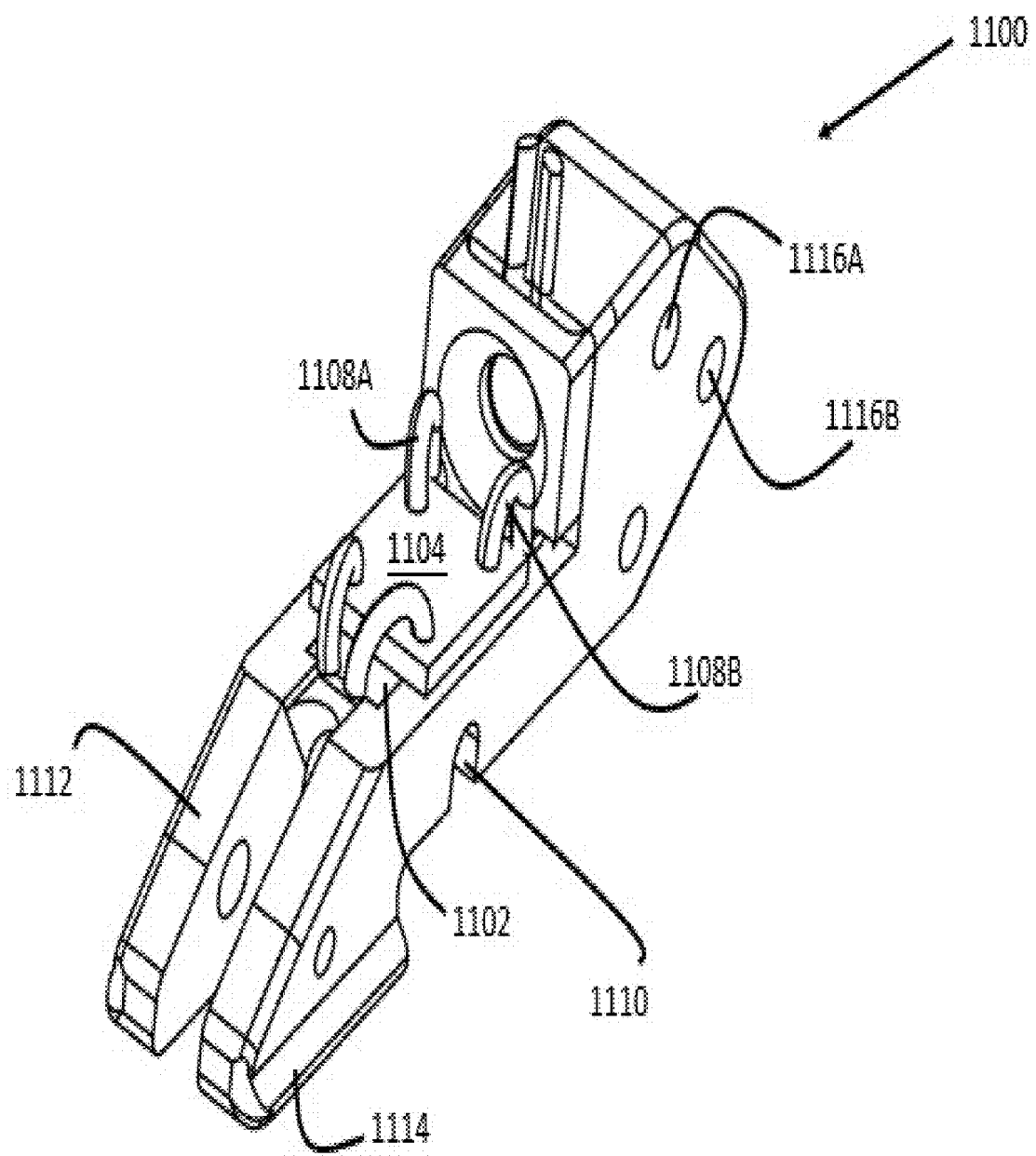
FIG. 11A shows an oblique view of a front finger follower in accordance with an example embodiment.
Figure 11B:
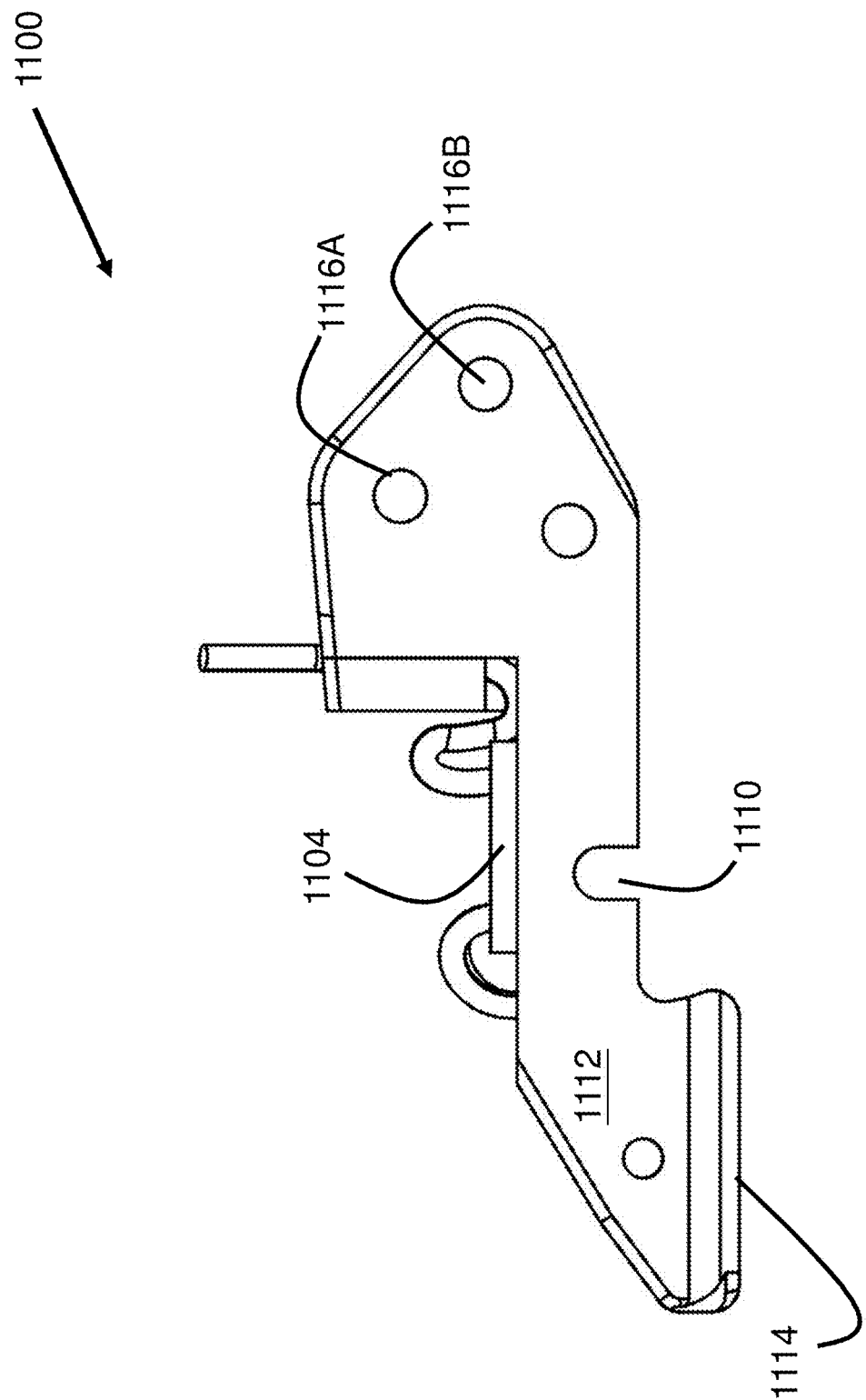
FIG. 11B shows a side view of a front finger follower in accordance with an example embodiment.

FIGS. 11A and 11B show a front finger follower 1100 in accordance with an example embodiment. A strain gauge sensor 1102 and a wire pad 1104 dispose on a flat section of the front finger follower 1100. By way of example, the strain gauge sensor is a film sensor.

In one example embodiment, the strain gauge sensor 1102 senses force signals generated by a finger of the user due to flexion/extension of the finger. The force signals then transmit through the first wires 1106A and 1106B to the wire pad 1104, and then transmits to a processor for analysis through second wires 1108A and 1108B.

In an example embodiment, the front finger follower 1100 includes a crack point 1110 disposed on a bottom side of the flat section of the front finger follower 1100. The crack point 1110 concentrates stress of the finger along a center line of the crack point 1110. When the finger presses, the crack point 1110 closes and the strain gauge sensor 1102 extends. When the finger extends, the crack point 1110 opens and the strain gauge sensor 1102 contracts.

In one example embodiment, the front finger follower 1100 includes a slanted proximal end 1112 and a finger pad 1114 or a strap holder is placed at a bottom side of the slanted proximal end 1112. By way of example, a strap holder is an intermediate strap holder 246 or a proximal strap holder 248 as shown in FIG. 2B.

Figure 2A:
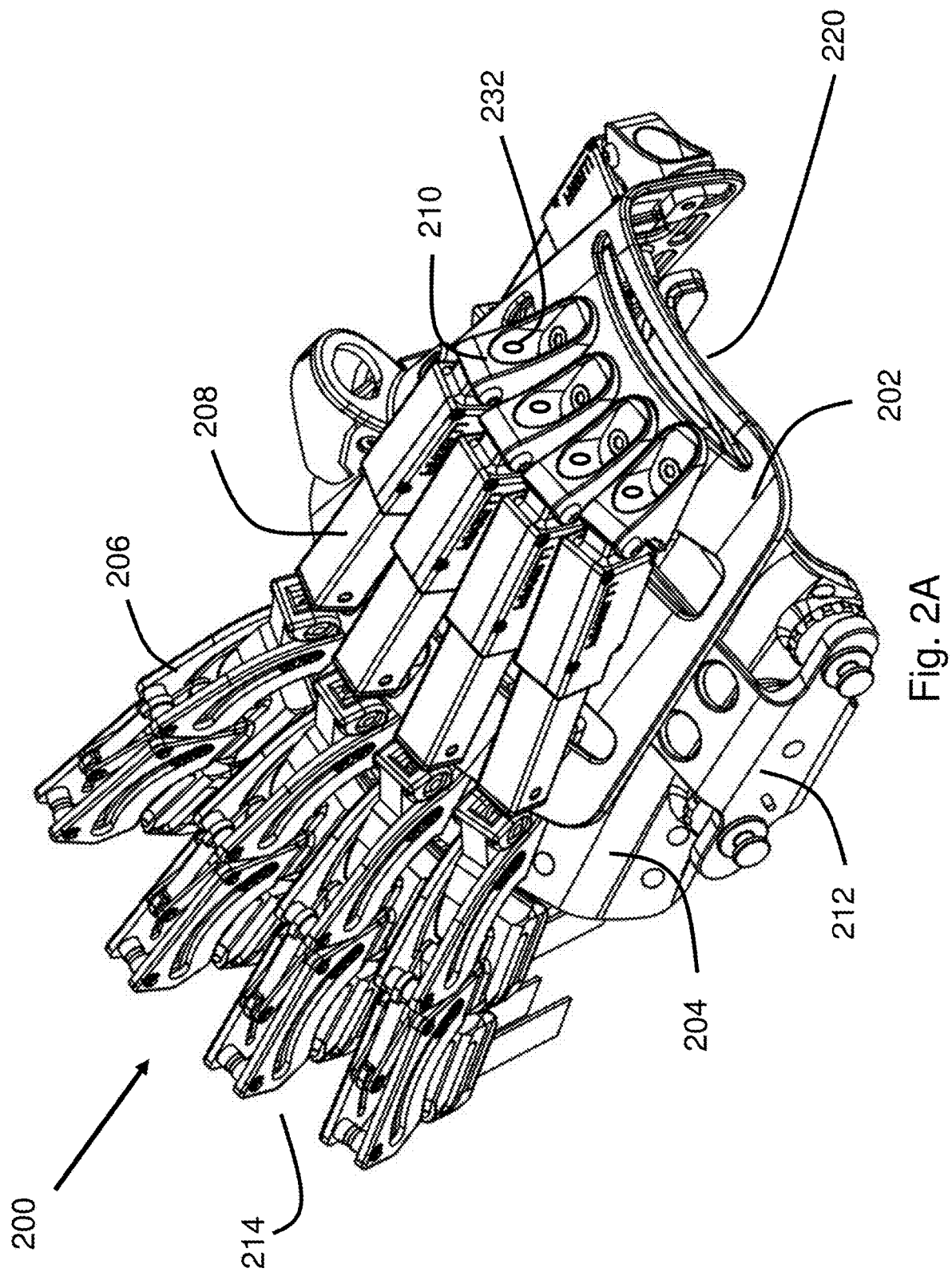
FIG. 2A shows a left perspective view of a dorsal side of a hand brace in accordance with an example embodiment.
Figure 2B:
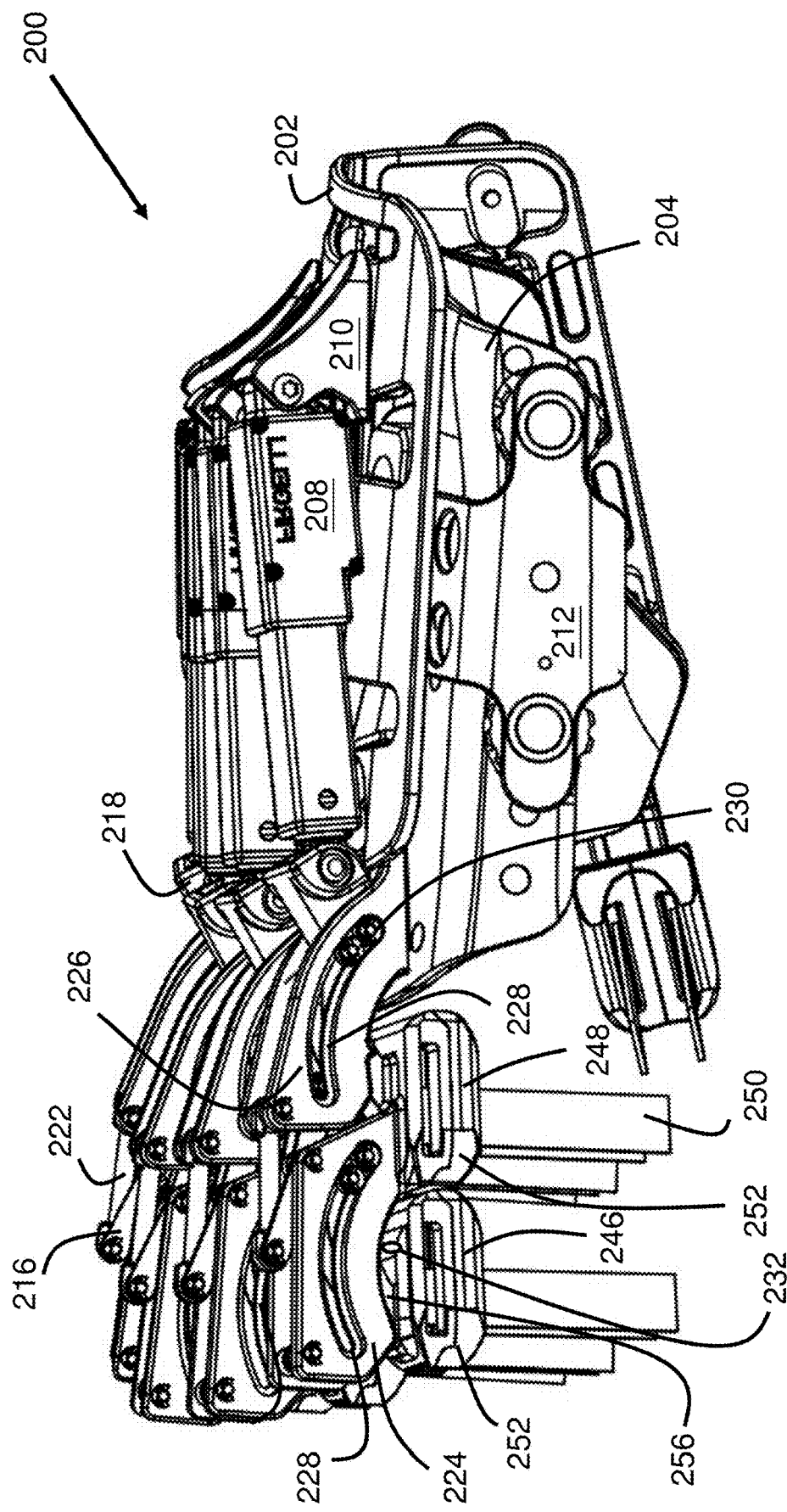
FIG. 2B shows a left side view of a hand brace in accordance with an example embodiment.
Figure 2C:
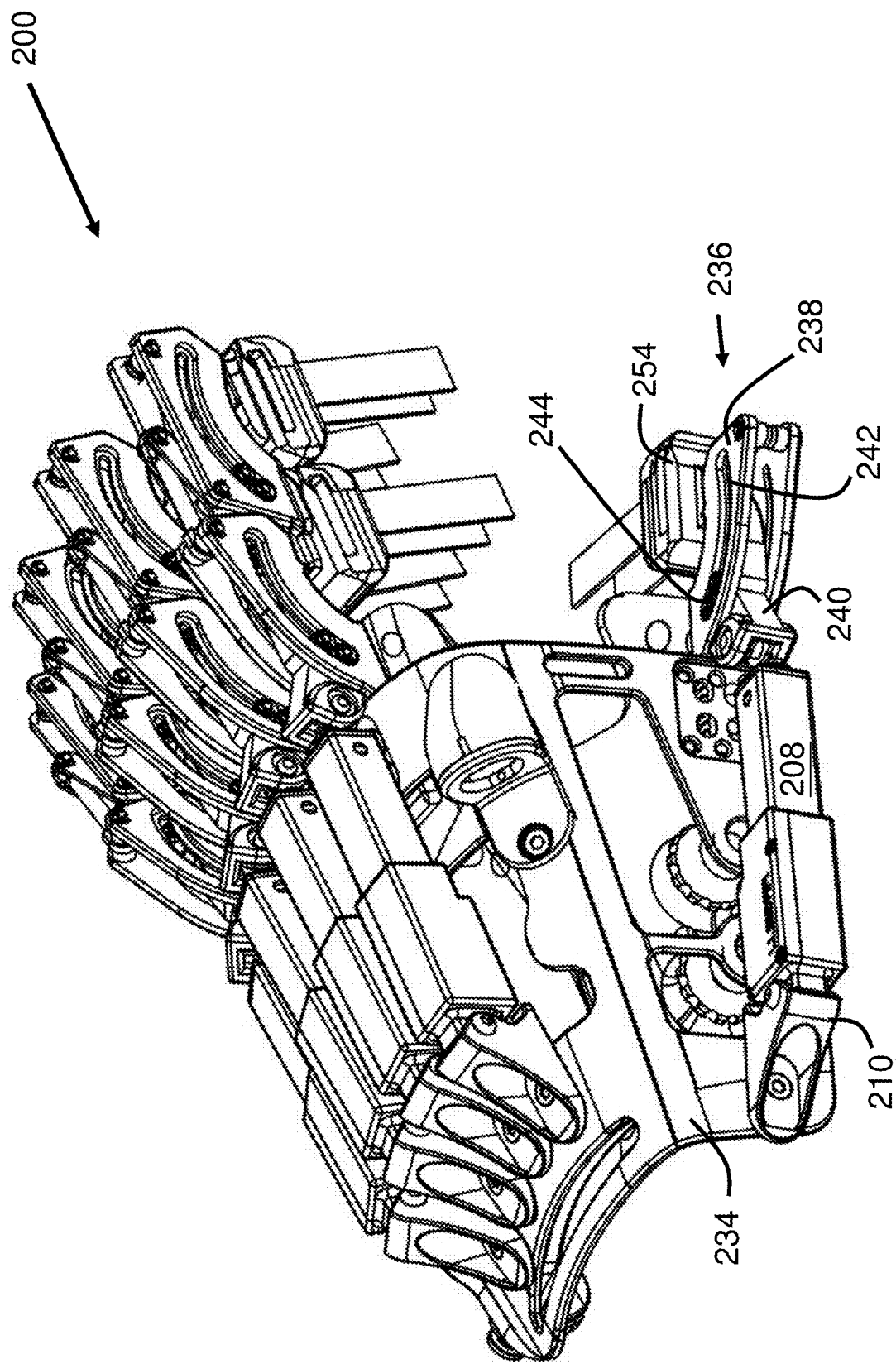
FIG. 2C shows a right side view of a hand brace in accordance with an example embodiment.

In another example embodiment, the front finger follower 1100 can rotate along a track (e.g. track 228 as shown in FIG. 2B) of a rail guide (e.g. an intermediate rail guide 224 as shown in FIG. 2B). By way of example, the rotational movement of the front finger follower 1100 is carried out by an interaction between a bearing that is movably disposed within a track (e.g. bearings 230 as shown in FIG. 2B) and holes 1116A to 1116B of the front finger follower 1100.

In an example embodiment, the strain gauge sensor 1102 measures a resultant force generated by the finger of the user. By way of example, the resultant force generated has a range of magnitude of 0-50 N.

Figure 2D:
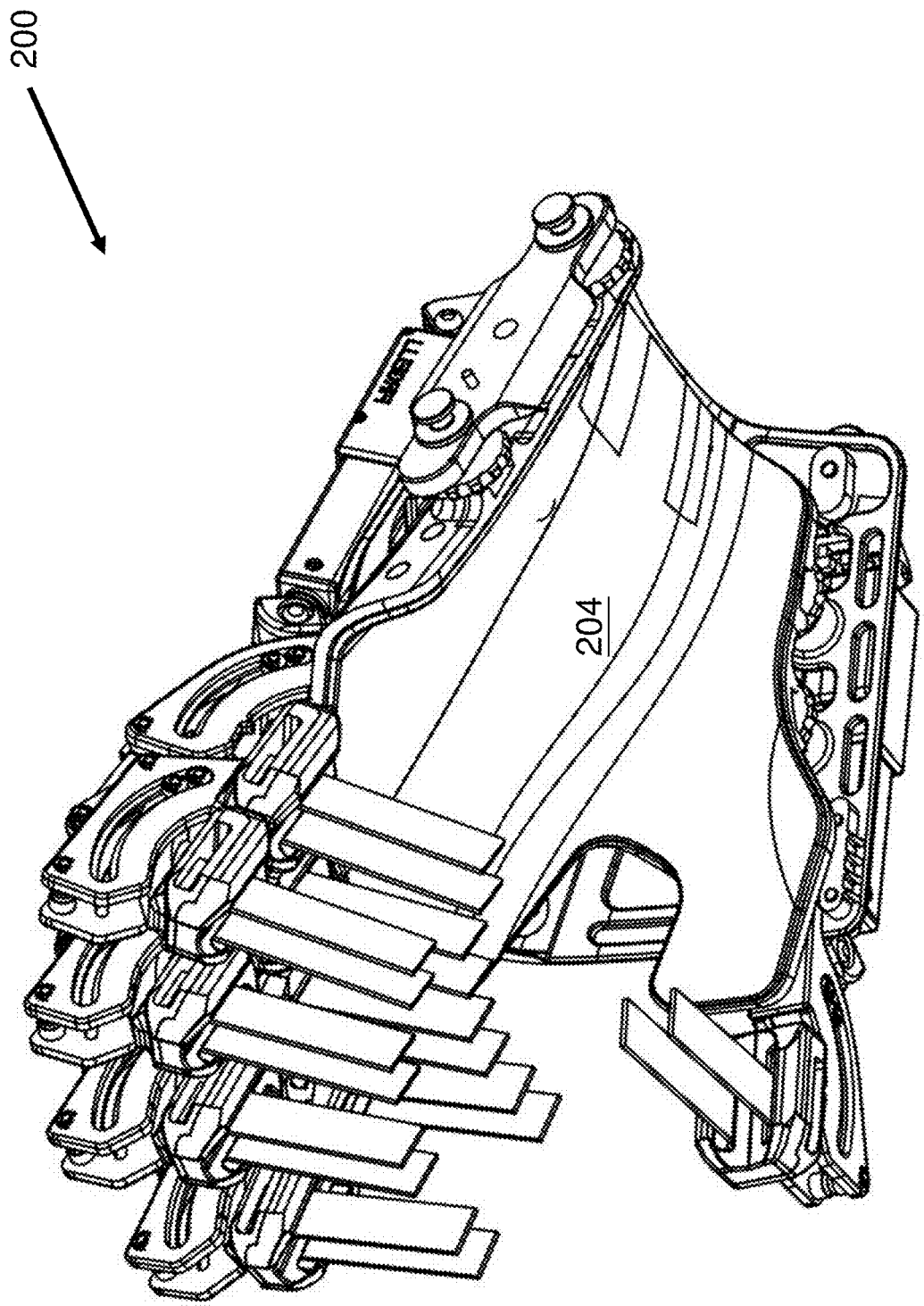
FIG. 2D shows a bottom view of a hand brace in accordance with an example embodiment.
Figure 12:
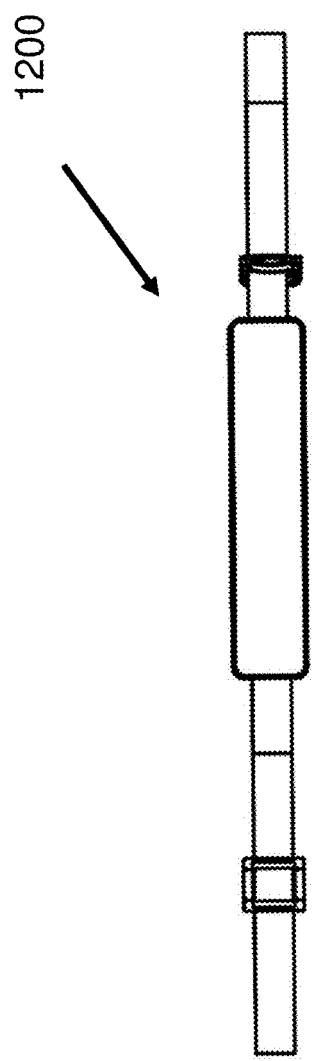
FIG. 12 shows a palm strap in accordance with an example embodiment.

FIG. 12 shows a palm strap 1200 in accordance with an example embodiment. In one example embodiment, the palm strap 1200 attaches to an internal platform of a hand brace (e.g. the internal platform 204 as shown in FIG. 2D) to fix a palm of user to the internal platform. By way of example, two palm straps are used to fix the palm to the internal platform more securely.

Figure 13A:
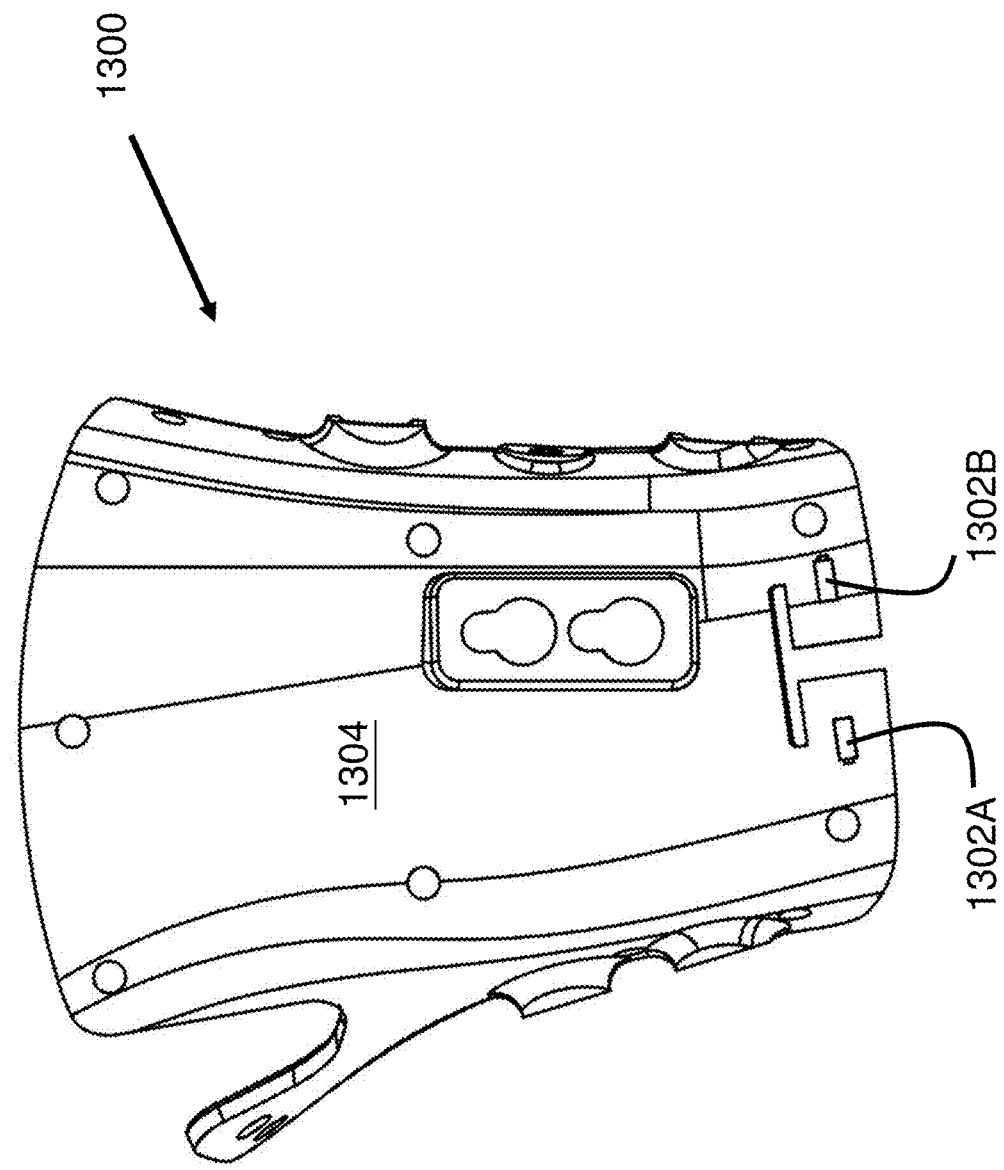
FIG. 13A shows a dorsal view of a hand brace platform in accordance with an example embodiment.

FIGS. 13A and 13B shows a hand brace platform 1300 in accordance with an example embodiment. In one example embodiment, the hand brace platform 1300 resembles an internal platform of a hand brace (e.g. the internal platform 204 as shown in FIG. 2D) that can be locked on an external platform of the hand brace (e.g. the external platform 202 as shown in FIG. 2A).

In one example embodiment, the hand brace platform 1300 includes brace strain gauge sensors 1302A and 1302B disposed on a first side 1304 of the hand brace platform 1300. The brace strain gauge sensors 1302A and 1302B detect force signals generated during supination and pronation.

In another example embodiment, the hand brace platform 1300 includes strain gauge pads 1306A and 1306B that are disposed on a second side 1308 of the hand brace platform 1300 and provide better sensation of the force generated during supination and pronation. Grooves are disposed on sides of the strain gauge pads 1304 and 1304B to create stress concentration therealong.

Examples of an EMG sensor include, but are not limited to, an EMG sensor, a MMG sensor, a combined sensor of EMG sensor and MMG sensor (i.e. an EMG-MMG sensor), a sensor in which a MMG sensor embeds between two EMG electrodes, and sensor includes two EMG electrodes with no MMG sensor.

As used herein, the term "connect" means that an element connects directly or indirectly to another element mechanically, electrically, or mechanically and electrically.

As used herein, an "actuator" converts electrical energy into mechanical energy to move finger assemblies. Examples of an actuator include, but are not limited to, linear actuator.

As used herein, a "wireless transmission" is the transmission of information between two points not connected by an electrical connector. Examples of wireless transmission include, but not limited to, wi-fi transmission, Bluetooth transmission, radio frequency (RF) transmission, infrared (IR) transmission and 3rd generation (3G) or 4th generation (4G) of mobile telecommunications technology.

The methods and apparatus in accordance with example embodiments are provided as examples, and examples from one method or apparatus should not be construed to limit examples from another method or apparatus. Further, methods and apparatus discussed within different figures can be added to or exchanged with methods and apparatus in other figures. Further yet, specific numerical data values (such as specific quantities, numbers, categories, etc.) or other specific information should be interpreted as illustrative for discussing example embodiments.

What is claimed is:

1. A method executed by a hand rehabilitation system to provide a training of finger flexion-extension and forearm supination-pronation to a user, the hand rehabilitation system comprising a power assistive hand rehabilitation device and a handheld portable device, the method comprising:

sensing, by a first set of two electromyography (EMG) sensors in the power assistive hand rehabilitation device, EMG signals of either finger flexion or finger extension of the user, wherein the first set of two EMG sensors are attached to a forearm of the user;

sensing, by a second set of two EMG sensors in the power assistive hand rehabilitation device, EMG signals of either forearm supination or forearm pronation of the user, wherein one of the second set of two EMG sensors is attached to an upper arm and the other one of the second set of two EMG sensors is attached to the forearm of the user;

sensing, by a strain gauge sensor in the power assistive hand rehabilitation device, force signals of a finger of the hand of the user;

receiving, by a processor in the power assistive hand rehabilitation device, an EMG onset time from the EMG signals, and a force onset time from the force signals;

analyzing, by the processor in the power assistive hand rehabilitation device hand rehabilitation system, the EMG onset time, and the force onset time to determine T0, T1, T2, and rate of force development (RFD) wherein said T0, T1, T2 and RFD indicate a time relationship of a complete muscle dynamics, wherein T0 is a time when an external stimulus is applied to the system, T1 is an onset time of the muscle dynamics and is determined by a mid-time that is a time halfway between the EMG onset time and the force onset time, T2 is an onset time of muscle force threshold and is determined when the force exceeds a force threshold, and RFD is a rate of change or development of the force calculated starting from the force onset time to the force threshold;

receiving, by a receiver in the power assistive hand rehabilitation device, from the handheld portable device, commands to actuate finger assemblies of the power assistive hand rehabilitation device for finger flexion-extension of the user and commands to rotate a rotatable platform of the power assistive hand rehabilitation device for forearm supination-pronation of the user, wherein the commands are generated in accordance with the determined time relationship of muscle dynamics;

actuating the finger assemblies and the rotatable platform of the power-assistive hand rehabilitation device to provide a training of finger flexion-extension and forearm supination-pronation to the user, wherein the forearm of the user rotates as a result of a rotational movement of the rotatable platform, and the forearm supination-pronation are exercised through the rotational movement of the rotatable platform along an inner circumferential surface of a C-shaped ring of the power assistive hand rehabilitation device; and controlling, by an actuator positioning controller in the power assistive hand rehabilitation device, a speed of the rotational movement of the rotatable platform.

2. The method of claim 1 further comprising:

storing, by a memory, the EMG signals, the force signals, the onset time of the muscle dynamics and movement histories of the power assistive hand rehabilitation device.

3. The method of claim 1, wherein five said gauge sensors are applied, in which each of the strain gauge sensors senses force signals of the finger where the each of the strain gauge sensors is located.

4. The method of claim 1, wherein the rotatable platform supinates from a neutral position to a maximum of 45 degrees of supination to an outer side with respect to the neutral position at the maximum supination position, and the rotatable platform pronates from the neutral position to a maximum of 90 degrees of pronation to an inner side with respect to the neutral position at the maximum pronation position, wherein the neutral position is a position where a thumb of the user faces upwards and is regarded as 0 degree.

5. The method of claim 1, wherein the speed of supination and pronation of the rotatable platform is controlled such that a cycle time of supination/pronation is the same as a cycle time of flexion/extension to achieve synchronization between the finger assemblies and the rotatable platform.

* * * * *